US011612669B2

(12) United States Patent
Chen et al.

(10) Patent No.: US 11,612,669 B2
(45) Date of Patent: Mar. 28, 2023

(54) DISINFECTION METHOD AND APPARATUS

(71) Applicants: University of Washington, Seattle, WA (US); Seattle Children's Hospital, Seattle, WA (US)

(72) Inventors: James Chen, Seattle, WA (US); Tanner Clark, Seattle, WA (US); Thomas Lendvay, Seattle, WA (US)

(73) Assignees: UNIVERSITY OF WASHINGTON, Seattle, WA (US); SEATTLE CHILDREN'S HOSPITAL, Seattle, WA (US)

(*) Notice: Subject to any disclaimer, the term of this patent is extended or adjusted under 35 U.S.C. 154(b) by 0 days.

(21) Appl. No.: 17/405,900

(22) Filed: Aug. 18, 2021

(65) Prior Publication Data

US 2022/0054672 A1 Feb. 24, 2022

Related U.S. Application Data

(60) Provisional application No. 63/074,280, filed on Sep. 3, 2020, provisional application No. 63/068,762, filed on Aug. 21, 2020.

(51) Int. Cl.
*A61L 2/08* (2006.01)
*A61L 31/12* (2006.01)
(Continued)

(52) U.S. Cl.
CPC .......... *A61L 2/088* (2013.01); *A41D 13/0002* (2013.01); *A41D 13/1192* (2013.01);
(Continued)

(58) Field of Classification Search
CPC . A61L 2/088; A61L 2/084; A61L 2/18; A61L 2/28; A61L 2202/26;
(Continued)

(56) References Cited

U.S. PATENT DOCUMENTS 3,817,389 A  6/1974 Weichselbaum
4,395,789 A  8/1983 Bruce
(Continued)

FOREIGN PATENT DOCUMENTS

CA  2276023 C  4/2002
CA  2473924 A1  7/2003
(Continued)

OTHER PUBLICATIONS

Chen, James, et al., "Vaccine Generation," U.S. Appl. No. 17/244,610, filed Apr. 29, 2021, 19 pages.
(Continued)

*Primary Examiner* — Timothy C Cleveland
(74) *Attorney, Agent, or Firm* — Christensen O'Connor Johnson Kindness PLLC

(57) ABSTRACT

Photosensitizers are incorporated into articles, such a personal protective equipment. A method of applying continuous and consistent light includes fitting the articles with light sources and optical fibers to apply light to the areas of the articles incorporated with the photosensitizers. Photosensitizers can be applied to articles by various applicators in either a gel or solution. A gel can be particularly effective when used on hydrophobic surfaces. Photodynamic reactor systems can be used to determine the effective doses of photosensitizers and the light dosimetry which can then be applied for use with the articles.

7 Claims, 11 Drawing Sheets

(51) Int. Cl.
  *A61L 31/16* (2006.01)
  *A41D 13/11* (2006.01)
  *A41D 13/00* (2006.01)
  *A41D 13/12* (2006.01)
  *A61L 2/28* (2006.01)
  *A61L 2/18* (2006.01)
  *A61L 101/44* (2006.01)

(52) U.S. Cl.
  CPC .............. *A41D 13/12* (2013.01); *A61L 2/084* (2013.01); *A61L 2/18* (2013.01); *A61L 2/28* (2013.01); *A61L 31/12* (2013.01); *A61L 31/16* (2013.01); *A61L 2101/44* (2020.08); *A61L 2202/11* (2013.01); *A61L 2202/122* (2013.01); *A61L 2202/14* (2013.01); *A61L 2202/26* (2013.01)

(58) Field of Classification Search
  CPC ........... A41D 13/0002; A41D 13/1192; A41D 13/12; A41D 13/1209
  See application file for complete search history.

(56) References Cited

U.S. PATENT DOCUMENTS

| | | | |
|---|---|---|---|
| 4,402,318 A | 9/1983 | Swartz | |
| 5,445,608 A | 8/1995 | Chen et al. | |
| 5,715,837 A | 2/1998 | Chen | |
| 5,741,316 A | 4/1998 | Chen et al. | |
| 5,766,234 A | 6/1998 | Chen et al. | |
| 5,782,896 A | 7/1998 | Chen et al. | |
| 5,814,008 A | 9/1998 | Chen et al. | |
| 5,827,186 A | 10/1998 | Chen et al. | |
| 5,830,526 A | 11/1998 | Wilson et al. | |
| 5,865,840 A | 2/1999 | Chen | |
| 5,997,569 A | 12/1999 | Chen et al. | |
| 6,080,160 A | 6/2000 | Chen et al. | |
| 6,096,066 A | 8/2000 | Chen et al. | |
| 6,210,425 B1 | 4/2001 | Chen | |
| 6,238,426 B1 | 5/2001 | Chen | |
| 6,273,904 B1 | 8/2001 | Chen et al. | |
| 6,281,611 B1 | 8/2001 | Chen et al. | |
| 6,319,273 B1 | 11/2001 | Chen et al. | |
| 6,331,744 B1 | 12/2001 | Chen et al. | |
| 6,344,050 B1 | 2/2002 | Chen | |
| 6,416,531 B2 | 7/2002 | Chen | |
| 6,454,789 B1 | 9/2002 | Chen et al. | |
| 6,520,669 B1 | 2/2003 | Chen et al. | |
| 6,580,228 B1 | 6/2003 | Chen et al. | |
| 7,018,395 B2 | 3/2006 | Chen | |
| 7,288,106 B2 | 10/2007 | Heacock et al. | |
| 7,320,786 B2 | 1/2008 | Chen | |
| 7,511,031 B2 | 3/2009 | Chen | |
| 7,802,572 B2 * | 9/2010 | Hahne ................ | A41D 13/1192 128/857 |
| 8,057,464 B2 | 11/2011 | Chen et al. | |
| 8,226,946 B2 | 7/2012 | Chen | |
| 8,450,359 B2 | 5/2013 | McCoy et al. | |
| 8,685,005 B2 | 4/2014 | Dahm et al. | |
| 8,685,071 B2 | 4/2014 | Burwell et al. | |
| 8,759,092 B2 | 6/2014 | Goodrich | |
| 9,149,651 B2 | 10/2015 | Keltner et al. | |
| 9,278,148 B2 * | 3/2016 | Fewkes ................ | G02B 6/0028 |
| 9,527,918 B2 | 12/2016 | Fiori et al. | |
| 10,307,610 B2 | 6/2019 | Keltner et al. | |
| 2003/0114434 A1 | 6/2003 | Chen et al. | |
| 2006/0223729 A1 | 10/2006 | Hamblin | |
| 2007/0038204 A1 | 2/2007 | Chen et al. | |
| 2007/0059316 A1 | 3/2007 | Pallenberg et al. | |
| 2007/0059791 A1 | 3/2007 | Goodrich | |
| 2007/0129776 A1 | 6/2007 | Robins et al. | |
| 2007/0133935 A1 | 6/2007 | Fine | |
| 2007/0142880 A1 | 6/2007 | Barnard et al. | |
| 2007/0286878 A1 | 12/2007 | Harruna | |
| 2008/0015189 A1 | 1/2008 | Hamblin | |
| 2008/0107636 A1 | 5/2008 | Goodrich | |
| 2009/0317436 A1 | 12/2009 | Wilson et al. | |
| 2010/0241054 A1 | 9/2010 | Dacey, Jr. et al. | |
| 2010/0274330 A1 | 10/2010 | Burwell et al. | |
| 2010/0305436 A1 | 12/2010 | Chen et al. | |
| 2011/0008372 A1 | 1/2011 | Chen | |
| 2011/0009464 A1 | 1/2011 | Chen | |
| 2011/0014239 A1 | 1/2011 | Goodrich | |
| 2011/0110818 A1 | 5/2011 | Mowbray-d'Arbela et al. | |
| 2012/0100039 A1 | 4/2012 | Appeaning et al. | |
| 2012/0209359 A1 | 8/2012 | Chen et al. | |
| 2014/0052050 A1 | 2/2014 | Courtin | |
| 2014/0303547 A1 | 10/2014 | Loupis et al. | |
| 2016/0091399 A1 | 3/2016 | Chen et al. | |
| 2016/0193338 A1 | 7/2016 | Loupis et al. | |
| 2016/0220728 A1 | 8/2016 | Adams et al. | |
| 2016/0270895 A1 | 9/2016 | Zoll | |
| 2017/0056603 A1 | 3/2017 | Cowan et al. | |
| 2018/0099063 A1 | 4/2018 | Lyons et al. | |
| 2018/0243790 A1 | 8/2018 | Grossman | |
| 2019/0161562 A1 | 5/2019 | Bakar et al. | |
| 2019/0314502 A1 | 10/2019 | Wei | |
| 2020/0315280 A1 | 10/2020 | Kaye | |

FOREIGN PATENT DOCUMENTS

| | | | | |
|---|---|---|---|---|
| CA | 2537235 | A1 | 1/2005 | |
| CN | 104589717 | B | 3/2017 | |
| CN | 208597758 | U | 3/2019 | |
| EP | 1644082 | A2 | 4/2006 | |
| EP | 1684865 | A1 | 8/2006 | |
| WO | 98/32494 | A1 | 7/1998 | |
| WO | WO-9949823 | A1 * | 10/1999 | ............. A01N 25/10 |
| WO | 2004/108249 | A1 | 12/2004 | |
| WO | 2005032459 | A2 | 4/2005 | |
| WO | 2006086770 | A2 | 8/2006 | |
| WO | 2008046019 | A1 | 4/2008 | |
| WO | 2014/130740 | A1 | 8/2014 | |
| WO | 2018/022926 | A1 | 2/2018 | |
| WO | 2019/183320 | A1 | 9/2019 | |

OTHER PUBLICATIONS

Chen, James, et al., "Antimicrobial Preventive Netting," U.S. Appl. No. 17/244,688, filed Apr. 29, 2021, 35 pages.
Shen, James, et al., "Photosensitizer Combination," U.S. Appl. No. 17/463,245, filed Aug. 31, 2021, 46 pages.
Chen, James, et al., "Invisible Singlet Film," U.S. Appl. No. 17/389,936, filed Jul. 30, 2021, 33 pages.
International Search Report and Written Opinion dated Nov. 8, 2021, issued in International Application No. PCT/US2021/046416, filed Aug. 18, 2021, 9 pages.
Lee, Im-Soon, et al. "Aerosol particle size distribution and genetic characteristics of aerosolized influenza A H1N1 virus vaccine particles." Aerosol and Air Quality Research 11.3 (2011): 230-237.
Meyer, Michelle, et al. "Aerosolized Ebola vaccine protects primates and elicits lung-resident T cell responses." The Journal of clinical investigation 125.8 (2015): 3241-3255.
Noimark, Sacha, et al. "Incorporation of methylene blue and nanogold into polyvinyl chloride catheters; a new approach for light-activated disinfection of surfaces." Journal of Materials Chemistry. 2012; 22(30): 15388-15396. <https://doi.org/10.1039/C2JM31987J>, 1 page.
Noimark, Sacha, Elaine Allan, and Ivan P. Parkin. "Light-activated antimicrobial surfaces with enhanced efficacy induced by a dark-activated mechanism." Chemical Science 5.6 (2014): 2216-2223.
Piccirillo, Clara, et al. "Antimicrobial activity of methylene blue and toluidine blue O covalently bound to a modified silicone polymer surface." Journal of Materials Chemistry 19.34 (2009): 6167-6171.
Fecht, S., "The First Fully 3-D Printed LEDs Are Here," 2014, <https://www.popsci.com/article/technology/first-fully-3-d-printed-leds-are-here/> [Accessed Mar. 24, 2020], 8 pages.
Waldman, Robert H., John J. Mann, and Parker A. Small. "Immunization against influenza: prevention of illness in man by aerosolized

(56) References Cited

OTHER PUBLICATIONS inactivated vaccine." Jama 207.3 (1969): 520-524. doi:10.1001/jama.1969.03150160032007, 1 page.

Fracalossi C, Nagata JY, Pellosi DS, et al. Singlet oxygen production by combining erythrosine and halogen light for photodynamic inactivation of Streptococcus mutans. Photodiagnosis and Photodynamic Therapy. 2016;15:127-132. https://search.datacite.org/works/10.1016/j.pdpdt.2016.06.011. doi: 10.1016/j.pdpdt.2016.06.011, 1 page.

Wood S, Metcalf D, Devine D, Robinson C. Erythrosine is a potential photosensitizer for the photodynamic therapy of oral plaque biofilms. Journal of antimicrobial chemotherapy. 2006;57(4):680-684.

Lee Y, Park H, Lee J, Seo H, Lee S. The photodynamic therapy on Streptococcus mutans biofilms using erythrosine and dental halogen curing unit. International journal of oral science. 2012;4(4):196-201.

Bhat M, Acharya S, Prasad K, Kulkarni R, Bhat A, Bhat D. Effectiveness of erythrosine-mediated photodynamic antimicrobial chemotherapy on dental plaque aerobic microorganisms: A randomized controlled trial. Journal of Indian Society of Periodontology. 2017;21(3):210-215.

Koshi E, Mohan A, Rajesh S, Philip K. Antimicrobial photodynamic therapy: An overview. Journal of Indian Society of Periodontology. 2011;15(4):323-327.

Akira Nakatsuma KK. Commentary on the phototoxicity and absorption of vitamin B2 and its degradation product, lumichrome. Pharmaceutica analytica acta. 2015;6(8). doi: 10.4172/2153-2435.1000403.

Makdoumi K, Hedin M, Bäckman A. Different photodynamic effects of blue light with and without riboflavin on methicillin-resistant Staphylococcus aureus (MRSA) and human keratinocytes in vitro. Lasers Med Sci. 2019;34(9):1799-1805.

Henneberry, B. How Surgical Masks are Made. Thomas Industry. <https://www.thomasnet.com/articles/other/how-surgical-masks-are-made/>[Accessed Mar. 21, 2020].

Clear Polypropylene Omnexus: The material selection platform. <https://omnexus.specialchem.com/centers/clear-polypropylene> [Accessed Mar. 21, 2020].

Almeida, A , et al. "Phage Therapy and Photodynamic Therapy: Low Environmental Impact Approaches to Inactivate Microorganisms in Fish Farming Plants," Marine Drugs 7(3): pp. 268-313, 2009.

Hasenleitner, M., et al. "In the Right Light: Photodynamic Inactivation of Microorganisms Using a LED-Based Illumination Device Tailored for the Antimicrobial Application," Antibiotics 9(1 ): pp. 1-13, 2020.

Trempolec, N., et al. "Photodynamic Therapy-Based Dendritic Cell Vaccination Suited to Treat Peritoneal Mesothelioma." Cancers 12.3 (2020): 545.

Weaver, E.A. "Dose Effects of Recombinant Adenovirus Immunization in Rodents," Vaccines 7(4):144 pp. 1-11, 2019.

Hankaniemi, M.M., et al. "A comparative study of the effect of UV and formalin inactivation on the stability and immunogenicity of a coxsackievirus B1 vaccine," Vaccine 37: pp. 5962-5971, 2019.

Mills, D., et al. "Ultraviolet germicidal irradiation of influenza-contaminated N95 filtering facepiece respirators," AJIC American Journal of Infection Control 46(7): pp. e49-e55, 2018.

Bull, J.J., et al. "Transmissible Viral Vaccines," Trends in Microbiology 26(1): pp. 6-15, Jan. 2018.

Barrett, P.N., et al. "Vero cell technology for rapid development of inactivated whole virus vaccines for emerging viral diseases," Expert Review of Vaccines 16(9): pp. 883-894, 2017.

Klasse, P.J. "Molecular determinants of the ratio of inert to infectious virus particles," Progress in Molecular Biology and Translational Science 129: pp. 285-326, 2015.

Klausberger, M. et al. "One-shot vaccination with an insect cell-derived low-dose influenza A H7 virus-like particle preparation protects mice against H7N9 challenge," Vaccine 32(3): pp. 355-362, 2014.

Mertes, P., et al. "Methylene blue-treated plasma: an increased allergy risk?" The Journal of Allergy and Clinical Immunology 130(3): pp. 808-812, 2012.

Seghatchian, J_ et al. "Main properties of the THERAFLEX MB-plasma system for pathogen reduction," Transfusion Medicine and Hemotherapy 38(1): pp. 55-64, 2011.

Marcus, P. et al. "In vitro analysis of virus particle subpopulations in candidate live-attenuated influenza vaccines distinguishes effective from ineffective vaccines," Journal of Virology 84(21): pp. 10974-10981, Nov. 2010.

Quan, F. et al. "Dose sparing enabled by skin immunization with influenza virus-like particle vaccine using microneedles," Journal of Controlled Release 147(3): pp. 326-332, 2010.

Victoria, J_ et al. "Viral nucleic acids in live-attenuated vaccines: Detection of minority variants and an adventitious virus," Journal of Virology 84(12): pp. 6033-6040, Jun. 2010.

Maves, R. et al. "Immunogenicity of a psoralen-inactivated dengue virus type 1 vaccine candidate in mice." Clinical and Vaccine Immunology 17(2): pp. 304-306, Feb. 2010.

Prausnitz, M.R., et al. "Microneedle-based vaccines," Current Topics in Microbiology and Immunology 333: pp. 369-393, 2009.

Geeraedts, F., et al. "Superior immunogenicity of inactivated whole virus H5N 1 influenza vaccine is primarily controlled by toll-like receptor signalling," PLoS Pathogens 4(8): p. e1000138, Aug. 2008.

Monath, T.P. et al. "A live, attenuated recombinant west nile virus vaccine," Proceedings of the National Academy of Sciences, USA 103(17): pp. 6694-6699, Apr. 25, 2006.

Meurice, F. et al. "Immunogenicity and safety of a live attenuated varicella vaccine (oka/SB bio) in healthy children," The Journal of Infectious Diseases 174(Supplement 3): pp. S324-S329, Nov. 1996.

THERAFLEX-MB Plasma-Processing Principle, advertisement published by MacoPharma, Sep. 2007.

"Influenza Vaccine," Cytiva, https://www.gelifesciences.com/en/us/solutions/bioprocessing/knowledge-center/influenza, vaccine-manufacturing [retrieved Mar. 30, 2020], 10 pages.

Borkar, T.G., et al. "Techniques Employed in Production of Traditional Vaccines Commonly Used by Military Forces: A Review," Journal of Archives in Military Medicine 7(102):e96149, pp. 1-12, Jun. 2019.

Plotino, G., et al. "Photodynamic therapy in endodontics," International Endodontic Journal (52): pp. 760-774, 2019.

Meller, D., et al. "Photodisinfection Therapy: Essential Technology for Infection Control," <https://infectioncontro.tips/2020/01/17/photodisinfection-therapy/> [retrieved Jul. 30, 2020], 20 pages.

What is Photodisinfection?, Ondine Biomedical, <https://ondinebio.com/technology> [retrieved Aug. 12, 2020], 5 pages.

Midden, R.W., Wang, S.Y., "Singlet Oxygen Generation for Solution Kinetics: Clean and Simple," Journal of the American Chemical Society, 105(13):4129-4135, Jun. 29, 1983.

Naito, K. et al. "Single-molecule detection of airborne singlet oxygen," Journal of the American Chemical Society 128(51): pp. 16430-16431, 2006.

Ogilby, P.R. "Singlet oxygen: There is indeed something new under the sun," Chemical Society reviews 39(8): pp. 3181-3209, 2010.

Zhao, Y. et al. "Singlet oxygen generation on porous superhydrophobic surfaces: Effect of gas flow and sensitizer wetting on trapping efficiency," The Journal of Physical Chemistry A 118(45): pp. 10364-10371, 2014.

Gao, R. et al. "Nano-photosensitizer based on layered double hydroxide and isophthalic acid for singlet oxygenation and photodynamic therapy," Nature communications 9(1):2798, pp. 1-10, 2018.

Felgentrager, A., et al. "Singlet oxygen generation in porphyrin-doped polymeric surface coating enables antimicrobial effects on Staphylococcus aureus," Physical Chemistry Chemical Physics:PCCP, 16(38): pp. 20598-20607, 2014.

Pushalkar, S. et al. "Superhydrophobic photosensitizers: Airborne 102 killing of an in vitro oral biofilm at the plastron interface," ACS Applied Materials & Interfaces 10(30): pp. 25819-25829, Jul. 4, 2018.

Hwang, J. et al. "Study of singlet oxygen dynamics on silicon polymer matrix," Journal of Analytical Methods in Chemistry vol. 2019 Article ID 2584686, pp. 1-6, Feb. 19, 2019.

(56) References Cited

OTHER PUBLICATIONS

Bartusik, D. et al. "Bacterial inactivation by a singlet oxygen bubbler: Identifying factors controlling the toxicity of 1O2 bubbles," Environmental Science & Technology 46(21): pp. 12098-12104, Oct. 18, 2012.

Aebisher, D. el al. "Superhydrophobic surfaces as a source of airborne singlet oxygen through free space for photodynamic therapy," ACS Applied Bio Materials 3(4): pp. 2370-2377, Mar. 17, 2020.

Boyce, John M. "Modern technologies for improving cleaning and disinfection of environmental surfaces in hospitals." Antimicrobial Resistance & Infection Control 5.1 (2016): 1-10.

Dancer, Stephanie J. "Controlling hospital-acquired infection: focus on the role of the environment and new technologies for decontamination." Clinical microbiology reviews 27.4 (2014): 665-690.

Pyrek, K. "Portable medical equipment: A significant source of transmission," Feb. 1, 2018, 16 pages.

Russotto, V., Cortegiani, A., Raineri, S. M., & Giarratano, A. Bacterial contamination of inanimate surfaces and equipment in the intensive care unit. Journal of Intensive Care. 2015;3(1):54, pp. 1-8.

Gabriele Messina, Emma Ceriale, Daniele Lenzi, Sandra Burgassi, Elena Azzolini, Pietro Manzi. Environmental contaminants in hospital settings and progress in disinfecting techniques. BioMed research international. 2013;2013:429780, 8 pages.

Bonetta S, Bonetta S, Motta F, Strini A, Carraro E. Photocatalytic bacterial inactivation by TiO2-coated surfaces. AMB Expr. 2013;3(1):1-8. https://www.ncbi.nlm.nih.gov/pubmed/24090112. doi: 10.1186/2191-0855-3-59.

Air permeable(breathable) film, <http://tamstech.net> [Accessed Mar. 25, 2020], 1 page.

Siracusa, Valentina. "Food packaging permeability behaviour: A report." International Journal of Polymer Science 2012 (2012), 2 pages.

Gahleitner, Markus, et al. Sterilization effects on polypropylene: technology and polymer type effects., Jan. 2003 , <https://www.researchgate.net/publication/288596501>, 3 pages.

"Cover Picture: Optik & Photonik Apr. 2015," Abstract, vol. 10, Issue 4, 2015,<https://doi.org/10.1002/opph.201590064>, 2 pages.

Molitch-Hou, M., "First 3D Printed Fiber Optics Created by University of Sydney researchers with Desktop 3d Printer," 2015, 3D Printing Industry, The Authority on Additive Manufacturing, <https://3dprintingindustry.com/news/first-3d-printed-fiber-optics-createdby-university-of-sydney-researchers-with-desktop-3d-printer-55047/> [Accessed Mar. 24, 2020], 1 page.

Ismail, Salim, et al. "Efficacy of a novel light-activated antimicrobial coating for disinfecting hospital surfaces." Infection Control & Hospital Epidemiology 32.11 (2011): 1130-1132.

International Search Report and Written Opinion dated Nov. 30, 2021, in International Application PCT/US2021/0046417, filed Aug. 18, 2021, 11 pages.

International Search Report and Written Opinion dated Dec. 6, 2021, in International Application PCT/US2021/046722, filed Aug. 19, 2021, 9 pages.

International Search Report and Written Opinion dated Feb. 2, 2022, issued in International Application No. PCT/US2021/046419, filed Aug. 18, 2021, 11 pages.

International Search Report and Written Opinion dated Feb. 1, 2022, issued in International Application No. PCT/US2021/048444, filed Aug. 31, 2021, 14 pages.

\* cited by examiner

DISINFECTION METHOD AND APPARATUS

CROSS-REFERENCE(S) TO RELATED APPLICATION(S)

This application claims the benefit of U.S. Provisional Application No. 63/068,762, filed Aug. 21, 2020 and U.S. Provisional Application No. 63/074,280, filed Sep. 3, 2020, both applications are incorporated herein expressly by reference.

BACKGROUND

In the medical setting, there are a multitude of hard or firm and relatively smooth surfaces, which routinely become continuously contaminated by a wide variety of pathogenic organisms such as viruses, bacteria, and fungi. Hard surfaces such as floors, walls, ceilings, windows, window sills, furniture, such as tables and chairs and stools, shelving and drawers, computer and laptop stands, other medical equipment stands, various types of medical and ancillary equipment needed directly or indirectly for patient care including, for example, medical charts, computer screens and monitors, food trays, lighting fixtures, IV poles, EKG monitors, hoses and tubing, exam tables, imaging equipment, bathroom fixtures, toilets, commodes, sinks, knobs and handles, IV bags and bottles, trash and infected waste containers, alcohol and soap dispensers, patient bed rails, phones, keyboards, and many other related items that are used in the medical setting require routine disinfection. Contamination of inanimate surfaces, products, and equipment by various pathogens occurs due to infected patients or other personnel harboring pathogenic microorganisms who spread and shed pathogens from their clothing, footwear, body surfaces, orifices, and from exhaled air, sputum, saliva, urine, feces, blood, sweat, by aerosolization, touch, and contact. Nosocomial infections are a leading cause of patient and healthcare worker (HCW) morbidity and mortality which tragically occurs on a regular basis. The intensive care unit is a particularly hazardous environment and pathogen contamination leads to high rates of patient morbidity and mortality. Means of disinfection include wiping and spraying of surfaces using various cleaning solutions and agents, exposure of surfaces to intense ultraviolet light, ozone, hydrogen peroxides, very hot steam, and the like.

Manual wiping and cleaning of surfaces has been found to be ineffective in studies due to poor technique, inadequate dwell time of the applied disinfectant, inadequate intrinsic antimicrobial activity of the disinfectant, over dilution of the disinfectant to be applied which reduces potency, inadvertent contamination of cleaning supplies, and missed application of the cleaning technique to all surfaces.

High intensity ultraviolet (UV) light is sometimes used. However, UV light delivered by a self-propelled or manually positioned device, or by a hand-held device has the drawbacks relating to safety, since UV light is highly injurious to the eyes and skin. For room disinfection, the room must be vacated by the patient and HCW, which is another disadvantage in a crisis situation, such as during viral epidemics and pandemics where every hospital bed is in use. Furthermore, patients in the intensive care unit may remain in the same room for weeks to months limiting the opportunity for use of such devices and techniques.

Aerosolized or vaporized hydrogen peroxide has also been trialed and may be associated with inadequate disinfection, may damage sensitive medical equipment left in the room, is associated with unacceptably prolonged cycle times and issues related to difficulty of venting the toxic gas safely, as well as danger to personnel from inadvertent leakage of toxic gas outside of the room.

Ozone generation has been proposed, but is fraught with similar, toxicities, danger, need for room clearance, and can cause corrosion, damaging sensitive medical equipment.

Steaming a room or corridor or large space is impractical and the heat and water vapor could damage sensitive medical equipment not intended to be waterproof. The risk of subsequent mold colonization is also a concern if materials are incompletely dried.

Titanium dioxide activated by ultraviolet light, produces a photocatalytic reaction, and titanium dioxide has been immobilized and incorporated into coatings and tiles for construction and building of rooms, however inadequate disinfection capability has been described, and its use in the medical setting is limited as a construction material. The requirement for UV light can also hamper its use.

During viral outbreaks and pandemics, wearing of facemasks by the public is a common activity. Both adults and children may wear facemasks indoors and outdoors, and the use of facemasks may be voluntary or required by local authorities. The commonly available and utilized facemasks which include surgical type of facemasks typically worn by the public can be purchased from various manufacturers and suppliers or constructed by persons from commonly available materials. A distinction is drawn between the N95 type of respirators manufactured to high level viral and pathogen barrier standards typically used by medical personnel and other types of facemasks which include surgical type of facemasks (public facemasks) with far lower barrier capacity commonly used by the public. In addition to viral high barrier capacity, the N95 respirators are intended to be specifically fit tested for specific individual users, which leads to a very tight fitting, highly face conforming mask which obviates air leak around the mask edges. Public facemasks by comparison are looser fitting, more comfortable, allow more normal air movement, air exchange, and respiration sensation, and allow air leakage around the edges of the facemask as a result. Compared to public facemasks, N95 type of respirators are commonly thicker, stiffer, and comprised of polymers specifically manufactured to enhance viral and particle barrier capacity. N95 type of respirators may also incorporate a hydrophobic surface coating or material in order to reduce fluid splashes and aqueous droplet penetration. Some public facemasks, especially surgical type of facemasks may also incorporate a hydrophobic outer layer as well.

Studies and research on the use of public facemasks during viral epidemics and pandemics has shown the public facemasks may reduce droplet ejection from the user, during normal respiration, or while sneezing or coughing. In contradistinction to the N95 type of respirators, the public facemask does little or nothing to protect the user from ambient droplet or aerosol inhalation. In other words, the public facemask may reduce contamination of the environment by a potentially infected user by capturing exhaled or expelled virus containing droplets, but does not protect the user from inhaling droplets already in the environment generated by other infected individuals, due to the lesser barrier function and air leakage around the public facemask edges.

In view of the conventional methods for disinfection and the drawbacks of facemasks, there is a need for additional methods for disinfection of surfaces and for enhancing the barrier function and reduce the infective potential from air leakage around the public facemask.

SUMMARY

An example of an article that is worn on a person comprises a material forming a part of the article that covers a body part, the material is configured to provide protection from microbes; and one or more photosensitizers are incorporated over an area of the material, wherein the one or more photosensitizers generate singlet oxygen by absorbing light of a particular waveband to provide protection from microbes in combination with the use of the material.

In an example, the article is a personal protective equipment article selected from a mask, a glove, and a gown.

In an example, the article further comprises one or more light source incorporated into the article, wherein the light source emits a waveband of light absorbed by the one or more photosensitizers.

In an example, the one or more light source includes a lens configured to direct the light onto the area of the material incorporated with the one or more photosensitizers.

In an example, the article further comprises one or more optical fiber that abuts the light source, wherein the optical fiber is an edge-emitting optical light fiber, and the edge-emitting optical light fiber emits light over the area of the material incorporated with the one or more photosensitizers.

In an example, the article further comprises a second light source incorporated into the article, wherein the second light source emits a waveband of light absorbed by the one or more photosensitizer, and the one light source emits light on a front of the material incorporated with the one or more photosensitizers, and the second light source emits light on a back of the material incorporated with the one or more photosensitizers.

In an example, the article further comprises two or more optical fibers that abut the one or more light source, wherein the two or more optical fibers are edge-emitting optical fibers, wherein at least one edge-emitting optical fiber is bound on a surface of the material incorporating the one or more photosensitizer and at least one edge-emitting optical fiber is within the material incorporating the one or more photosensitizer.

In an example, the article further comprises one or more light sources and one or more edge-emitting optical light fibers incorporated into the article, the one or more light sources and one or more edge-emitting optical fibers emit light over substantially an entire area of the material incorporated with the one or more photosensitizers, and the light includes a waveband of light that is absorbed by the one or more photosensitizers.

In an example, the material is an optically transparent polymer.

An example of a method of disinfecting an article comprises loading a composition onto an absorbent material via diffusion of the composition from a reservoir connected to the absorbent material, the composition includes one or more photosensitizers in a solution or gel; and applying the composition onto an area of an article by placing the absorbent material in contact with the article.

In an example, the composition including the one or more photosensitizers is a gel, and the method further comprises applying the gel onto a hydrophobic material of the article.

An example of a disinfecting gel composition comprises one or more photosensitizers, each photosensitizer has a concentration from 0.01 µM to 1,000 µM; a gelling agent selected from agar, pectin, carrageenan, guar gum, locust bean gum, gelatin, and combinations thereof, each gelling agent has a concentration; and a diluent or solvent.

In an example, the one or more photosensitizers are selected from the group consisting of methylene blue, riboflavin erythrosine, methylene blue derivatives, riboflavin derivatives, erythrosine derivatives, and combinations thereof.

In an example, the disinfecting composition further comprises an alcohol.

An example of a system for photodynamically treating microbes comprises a vessel containing a liquid photosensitizing composition of one or more photosensitizers within an interior of the vessel; a light source configured to direct light to the interior of the vessel, the light source is configured to emit light in a red waveband, light in a blue waveband, and light in a green waveband; and the light source is configured to vary fluence rates of the wavebands; and a controller the controls the wavebands emitted by the light source and fluence rates emitted by the light source.

In an example, the light source includes one or more RGB light emitting diodes.

In an example, the controller includes a memory having stored thereon values of absorption wavebands for the one or more photosensitizers.

In an example, the light source is external to the vessel, and the light from the light source is directed to the interior of the vessel by one or more optical fibers.

In an example, the vessel includes sides made from optically clear material, the light source is external to the vessel, the light source is stationary and directed at the vessel, and the vessel is configured to rotate to pass by the light source.

In the examples herein, the one or more photosensitizers include one or more of methylene blue derivative, methylene blue, xanthene dyes and derivatives, chlorophyll derivatives, tetrapyrrole structures, porphyrins, chlorins, bacteriochlorins, phthalocyanines, texaphyrins, prodrugs, aminolevulinic acids, phenothiaziniums, squaraine, boron compounds, transition metal complexes, hypericin, riboflavin, curcumin, titanium dioxide, psoralens, tetracyclines, flavins, riboflavin, riboflavin derivatives, erythrosine, erythrosine derivatives, photosensitizer nanocompositions, or combinations thereof.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
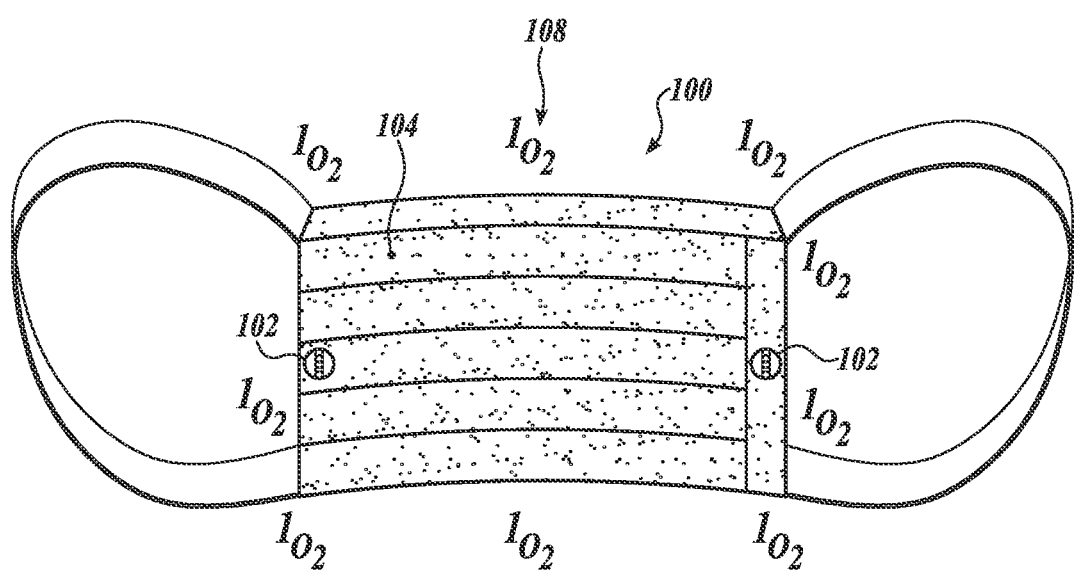
FIG. 1 is a diagrammatical illustration of a facemask in accordance with one embodiment.

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the FIGURES should not be viewed as limiting. It should be understood other embodiments may include more or less of each element shown in a given FIGURE. Further, some of the illustrated elements may be combined or omitted. Yet further, an example embodiment may include elements not illustrated in the FIGURES. As used herein, with respect to measurements, "about" means +/−5%. As used herein, with respect to denoting a portion of, a fraction of, and the like, "substantially" can include at least 50%, or at least 60%, or at least 70%, or at least 80%, or at least 90%, or at least 95%, or at least 98%.

Some of the embodiments disclosed herein and in materials attached and appended to this application are related to methods and apparatus for disinfecting medical equipment. Generally, the medical equipment being disinfected by the methods and apparatus are personal protective equipment, for example, that may have otherwise been designed as items for single use and/or disposable equipment.

The current disclosure details apparatus and methods of use based on photodynamic therapy that is an effective disinfection technique with demonstrated utility against microbes, such as viruses and other pathogens.

It shall be understood that the term "microbial," "microbe," and variations, as used herein, refers to an infectious microorganism, pathogen, or agent, including one or more of a virus, viroid, bacterium, archaea, protists, protozoan, prion, fungus, toxin, or the like. Further, it shall be understood that the term "immunogen", as used herein refers to an antigen or any other substance that induces both an immune response by a patient's immune system and generation of antibodies that bind to the immunogen.

Photodynamic therapy uses one or more photosensitizers activated by light of any waveband, including, for example, visible light, UV, and infrared. Photosensitizers may have peak absorption of light at specific wavebands. In the examples, photosensitizers include, but are not limited to, all types of methylene blue derivatives and methylene blue itself, xanthene dyes and derivatives, chlorophyll derivatives, tetrapyrrole structures, porphyrins, chlorins, bacteriochlorins, phthalocyanines, texaphyrins, prodrugs such as aminolevulinic acids, phenothiaziniums, squaraine, boron compounds, various transition metal complexes, hypericin, riboflavin, curcumin, titanium dioxide, psoralens, tetracyclines, flavins such as riboflavin, riboflavin derivatives, erythrosine, erythrosine derivatives, photosensitizer nanocompositions, and the like. Combinations of two or more of any of the mentioned photosensitizers are suitable for this disclosure. In some examples, preferred photosensitizers are a combination of ones that are generally recognized as safe, and that are capable of absorbing light over a wide spectral range, such as, for example, a combination of erythrosine, methylene blue, and riboflavin.

The apparatus and methods can also include nanocompositions of photosensitizers and photosensitizers linked to a variety of other substances which may improve the photodynamic inactivation process including but not limited to crystal violet, gold nanoparticles, and the like. For example, methylene blue can be modified into a covalently loaded polyacrylamide nanoparticle structure which has photodynamic activity, and which may permit easier incorporation into masks, respirators, and personal protective equipment.

A photosensitizer can generate at least singlet oxygen in response to light provided at particular wavebands or wavelengths and for a particular duration. Singlet oxygen is known by the chemical formula, $^1O_2$.

Different photosensitizers are triggered to produce singlet oxygen or other radicals by different wavebands or wavelengths of light. Any light source can be used that emits the proper wavebands or wavelengths of light that are effectively absorbed by the photosensitizer leading to singlet oxygen generation. Light sources may include, but are not limited to, light emitting diodes (LED), xenon lamps, fluorescent bulbs and tubes, incandescent light bulbs, electroluminescent devices, lasers, and the like. Other known or contemplated light sources are not excluded and include all known wavelengths and wavebands known to lead to a photodynamic effect particular to the photosensitizer agent. In some embodiments, the light source is not an artificial light source and can include natural light, i.e., sunlight.

Compositions including photosensitizers may be provided in solutions, gels, and powder (e.g. dry). The compositions may include one or more excipients in addition to one or more photosensitizer. Photosensitizers can be included in such compositions in concentrations ranging from 0.01 µM to 1,000 µM. When two are more photosensitizers are combined, each photosensitizer can have a concentration from 0.01 µM to 1,000 µM.

When describing photosensitizers used with articles, methods, or in compositions, the molar concentration of each of the one or more photosensitizers also include values in the range of 0.01 µM to 1,000 µM, such as, but not limited to, 0.01 µM, 0.02 µM, 0.03 µM, 0.04 µM, 0.05 µM, 0.06 µM, 0.07 µM, 0.08 µM, 0.09 µM, 0.1 µM, 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, and 1,000 µM.

Photosensitizers mixed in solutions may include solvents or diluents, including water, alcohol, or both. Photosensitizers in gels may include solvents, diluents, with at least one or more gelling agents, as further described below. The photosensitizer compositions can be applied to articles and surfaces which allows volatile solvents or diluents to evaporate leaving the photosensitizer and any nonvolatile compound.

The illumination time to generate singlet oxygen from photosensitizers can be determined empirically, experimentally, or derived from known data. For example, one micromolar solution of methylene blue, activated by white light at 45,000 lux for more than one hour can inactivate microbes, viruses, and bacteria in blood plasma. In one example, an effective amount of light corresponds to an exposure time that can range from 1 second to 2 hours, and the lux (lumen per square meter) can range from 10 to 50,000. In one example, a preferred exposure time is from 1 minute to 1 hour and a lux range from 100 to 10,000. In one example, the most preferred exposure time is from 5 minutes to 30 minutes, and a lux range from 100 to 10,000. In one example, the fluence rate of light or of any waveband can range from 1-200 mW/cm$^2$. In the examples, one or more of the light parameters can be adjusted.

FIGS. 1, 2, 3, and 4 illustrate examples of articles, such as personal protective equipment, that are impregnated with one or more photosensitizers 104. In the FIGS. 1, 2, 3, and 4 like numbers are used to represent like parts. Although articles of personal protective equipment are illustrated, it should be understood the examples are representative, and other articles of clothing can be used, in addition to the application of photosensitizers to surfaces of any apparatus and objects.

In one example, an article used for personal protection equipment incorporates material as part of the article that is used for covering a body part to be protected, the material is configured to provide protection from microbes, and one or more photosensitizers are incorporated over an area of the material, wherein the one or more photosensitizers generate singlet oxygen by absorbing light of a particular waveband to provide protection from the microbes in combination with the use of the material.

In one example, at least one photosensitizer 104 with optional inclusion of other excipients is applied to the masks or respirators 100, 200, gloves 300, gowns 400, and other PPE. In examples, the one or more photosensitizer 104 is impregnated onto areas of materials that provide for protection against microbes, viruses, and the like. For example, masks and gloves are smaller articles that can have photosensitizer 104 impregnated onto the whole of their exterior surfaces, while gowns being larger can have photosensitizer 104 impregnated onto the exterior front only, for example.

After impregnation with the photosensitizer 104, the articles can be illuminated with either with natural or artificial light to generate at least singlet oxygen 108. In examples, the surfaces of the masks, respirators, gloves, gowns, and PPE to be disinfected by the light and photosensitizer combination can be illuminated in a continuous manner by the use of lights 102 attached to the articles. Here, the materials of the masks or respirators 100, 200, gloves 300, gowns 400, and other PPE that are impregnated with the photosensitizer 104 can extend over a significant area, or the material can bend and fold, thus, the light may not reach some of the areas that are impregnated with the photosensitizer 104. In one example, one or more light sources 102 can be positioned at different locations on the articles to illuminate significantly all the areas of the material that are impregnated with the photosensitizer 104.

In examples, one or more edge-emitting optical fibers 106 are used to carry the light to significantly all the areas of the material that are impregnated with the photosensitizer 104.

In the examples, the masks 100, 200, glove 300, and gown 400 impregnated with photosensitizer 104 can include one or more artificial light source 102 incorporated on or within the mask, glove, or gown. The light from the light source 102 generates singlet oxygen 108 from the photosensitizer 104.

In examples, the masks 100, 200, gloves 300, and gowns 400 impregnated with photosensitizer 104 can include one or more artificial light source 102 incorporated on or within the mask, glove, or gown and one or more edge-emitting fibers 106 and/or end-emitting light fibers to carry the light to areas of the materials impregnated with the photosensitizer 104. The light from the light source 102 and any edge-emitting 106 and end-emitting optical fibers generates singlet oxygen 108 from the photosensitizer 104.

In examples, the masks 100, 200, glove 300, and gown 400 impregnated with photosensitizer 104 are exposed to sunlight, which generates the singlet oxygen 108 to inactivate viruses or other pathogens in the absence of an embedded light source on the PPE article itself.

In examples, the photosensitizer 104 can include at least methylene blue, and the light source 102 can include a red LED which efficiently activates methylene blue. In examples, the methylene blue or other photosensitizer is incorporated into the masks or respirator 100, 200, glove 300, gown 400, or PPE during its manufacture, or applied as a coating or in solution. In examples, the LED 102 can be a RGB (red-green-blue) LED to emit any waveband comprised in white light. An RGB LED can produce light to emit generally any waveband of light that could be absorbed by the particular photosensitizer 104.

The semiconductor material used in the LED 102 will affect the wavelength produced by the LED. Semiconductor materials for LEDs can include, for example, gallium phosphide for red, yellow, and green wavebands, aluminum gallium phosphide and gallium nitride for green and ultraviolet wavebands, gallium arsenide phosphide for red and orange wavebands, aluminum gallium arsenide phosphide for red, orange, and yellow wavebands, indium gallium nitride and zinc selenide for blue wavebands. Other semiconductors to achieve a certain waveband are known in the literature.

In examples, the one or more of the LEDs 102 can be powered by a small battery that is attached or bonded to at least one edge of the mask and illuminates one or both mask surfaces simultaneously. In examples, the one or more LEDs 102 are positioned such that the emitted light illuminates the entire mask or respirator 100, 200, glove 300, gown 400, or other PPE surface. In examples, at least one small battery powered LED light of any wavelength from ultraviolet to infrared, which has an incorporated clip can be clipped to the mask or respirator 100, 200, glove 300, gown 400 or other PPE. In examples, the battery can be incorporated into the LED assembly as a single unit with a clip or be worn behind the ear as in a hearing aid or hanging from the neck and connected to at least one LED or LED array by electrical wires.

In examples, the one or more LEDs 102 can have directional lenses that direct the light over the areas of material impregnated with the photosensitizer 104. Preferably, the inner and outer surfaces of the mask or respirator 100, 200, glove 300, gown 400, or other PPE equipment is illuminated simultaneously so as to provide continuous photodynamic and light activated disinfection. Continuous illumination can provide the advantage of continuous disinfection as continued exposure to the virus or other pathogen occurs.

Figure 9:
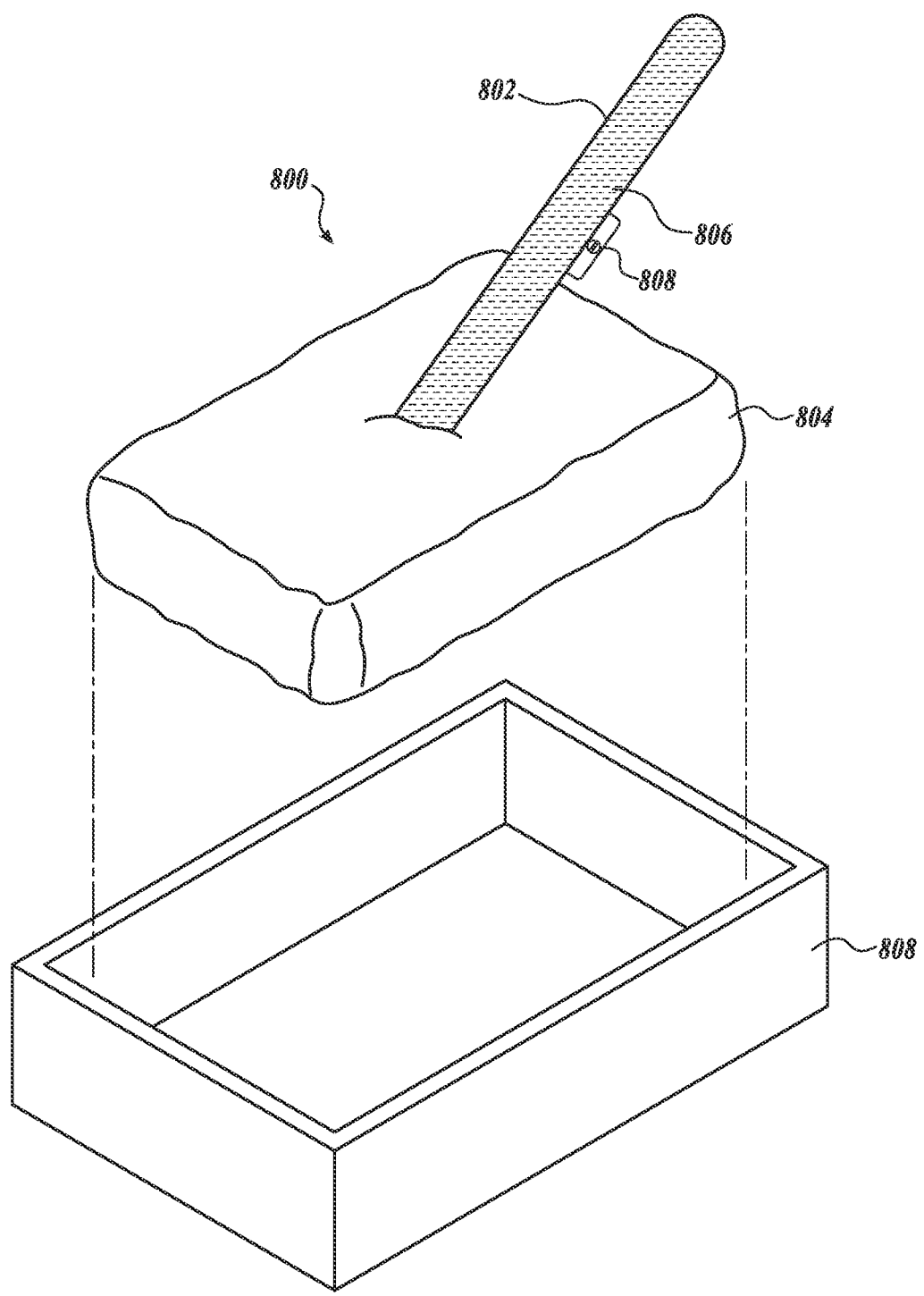
FIG. 9 is a diagrammatical illustration of an applicator in accordance with one embodiment.
Figure 10:
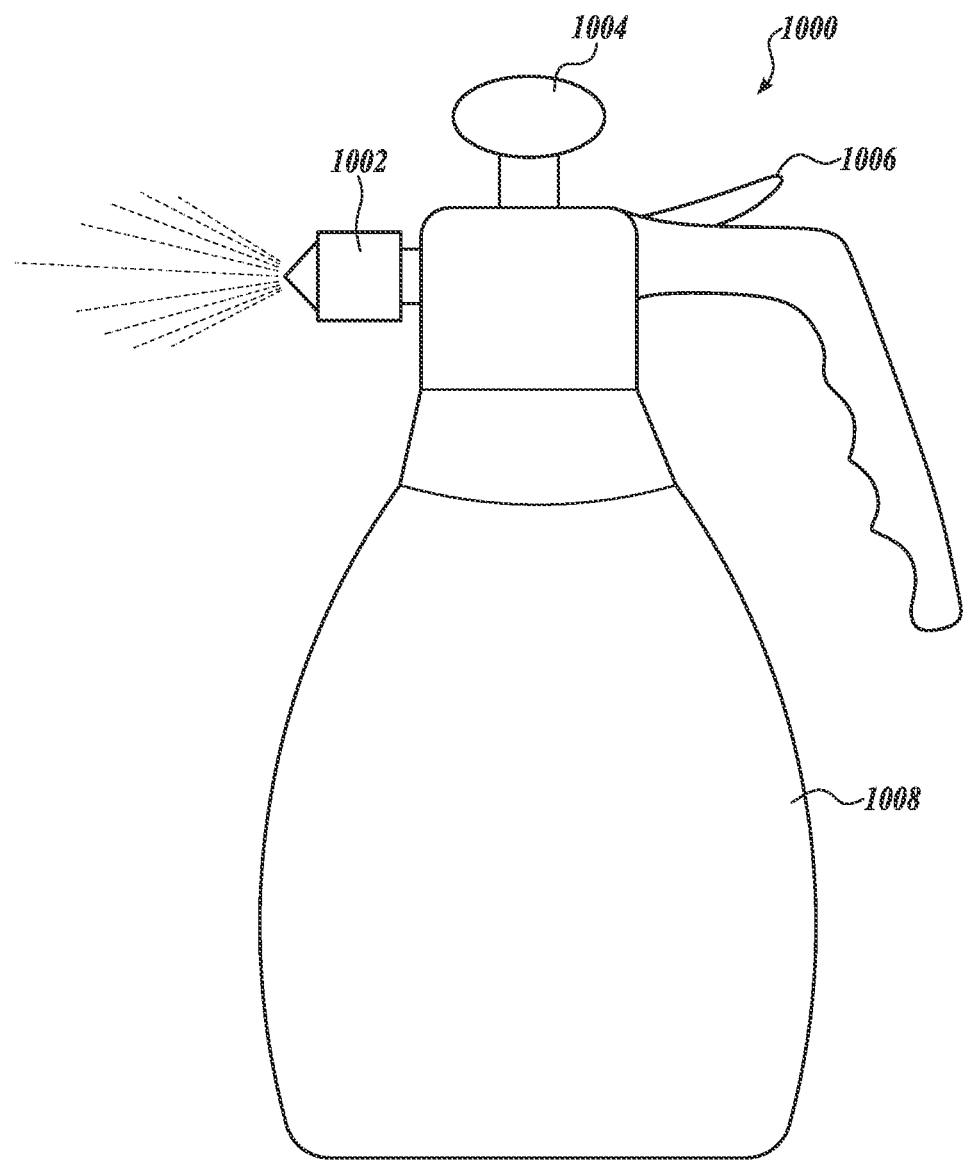
FIG. 10 is a diagrammatical illustration of an applicator in accordance with one embodiment.
Figure 11:
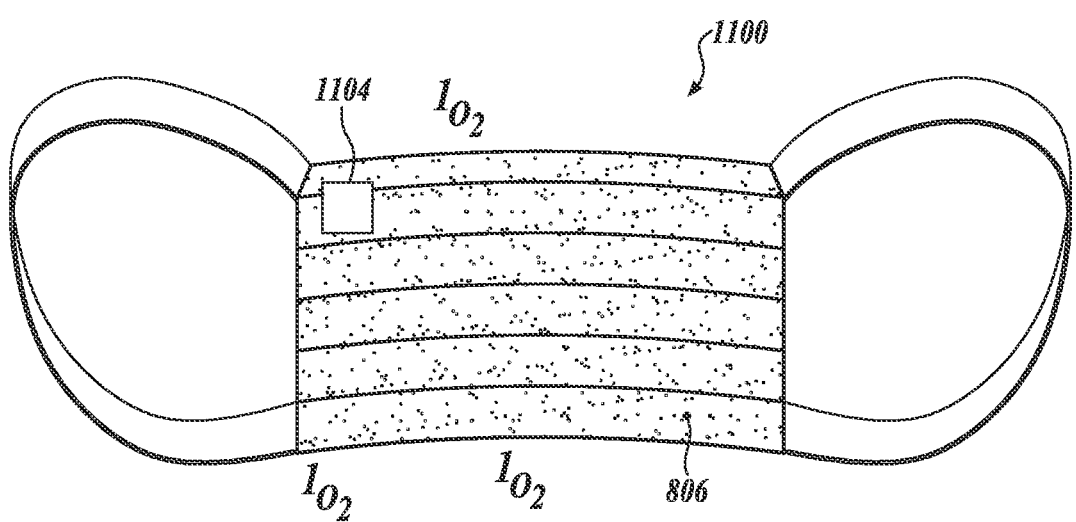
FIG. 11 is a diagrammatical illustration of a photosensitizer indicator in accordance with one embodiment.

In examples, the one or more photosensitizer 104 are applied onto the mask or respirator 100, 200, glove 300, gown 400, or other PPE by the applicators described herein with relation to FIGS. 9 and 10. However, any application method can be used including dipping the articles into a bath of photosensitizer solution. In examples, the one or more photosensitizer 104 can placed into a solution, for example saline or other biocompatible liquid which may also contain an antiviral agent such as alcohol or other compatible substances and then applied onto the surface of a contaminated on non-contaminated mask, glove, or gown, or other PPE. In examples, an optically transparent gel can be used in the applicators which may contain alcohol or other known antiviral and antimicrobial substances in addition to the photosensitizer, which is applied to the mask, glove, gown, or other PPE.

In the application of the photosensitizer 104, the concentration of photosensitizer 104 over an area, and the required light intensity, waveband, or wavelength, and illumination time for the required disinfection can be determined experimentally. As an example, concentrations ranging from 0.01 µM to 1,000 µM may be suitable. The concentration, light parameters, and illumination time, for example, can be tested in a microbiology and/or virology laboratory. A photodynamic reactor system for such purpose is disclosed herein with reference to FIGS. 7 and 8. For example, a virus or other pathogenic organism containing solution can be placed on a material sample or actual mask, glove, gown or other PPE and exposed to varying photosensitizer concentrations and varying light doses in a laboratory setting in order to determine the required effective drug and light dose. The treated material can be swabbed or otherwise prepared for viral or microbial viability testing.

In an example, the one or more photosensitizer 104 is incorporated and otherwise embedded into and throughout the personal protective equipment as part of the manufacturing process. This example enables any virions or microbial pathogens which penetrate, for example, the mask surface to be inactivated by light exposure. A drawback of some masks is improper or poor fit which permits airborne pathogen exposure under the mask. At least some airborne pathogen which travels to the undersurface of a mask will be exposed to the photosensitizer coating the underside of the mask surface, where it can be disinfected, thus potentially lowering the exposure risk to the user.

In examples, the one or more photosensitizer 104 can be applied intermittently during use of the mask or respirator, glove, gown, or other PPE in order to continually enhance the photodynamic disinfection process during use by a healthcare worker.

Figure 2:
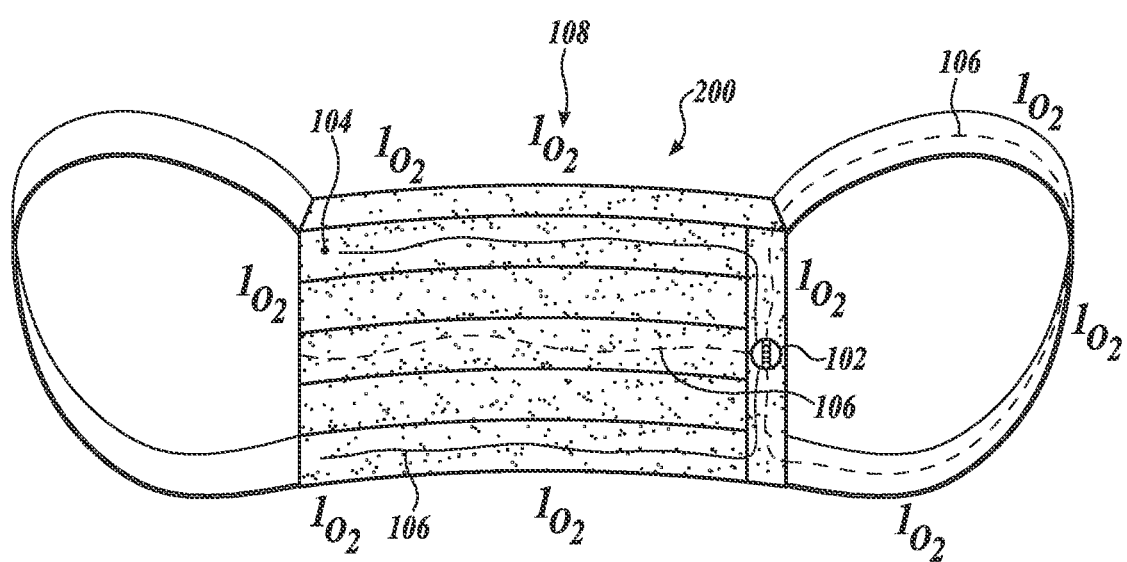
FIG. 2 is a diagrammatical illustration of a facemask in accordance with one embodiment.
Figure 3:
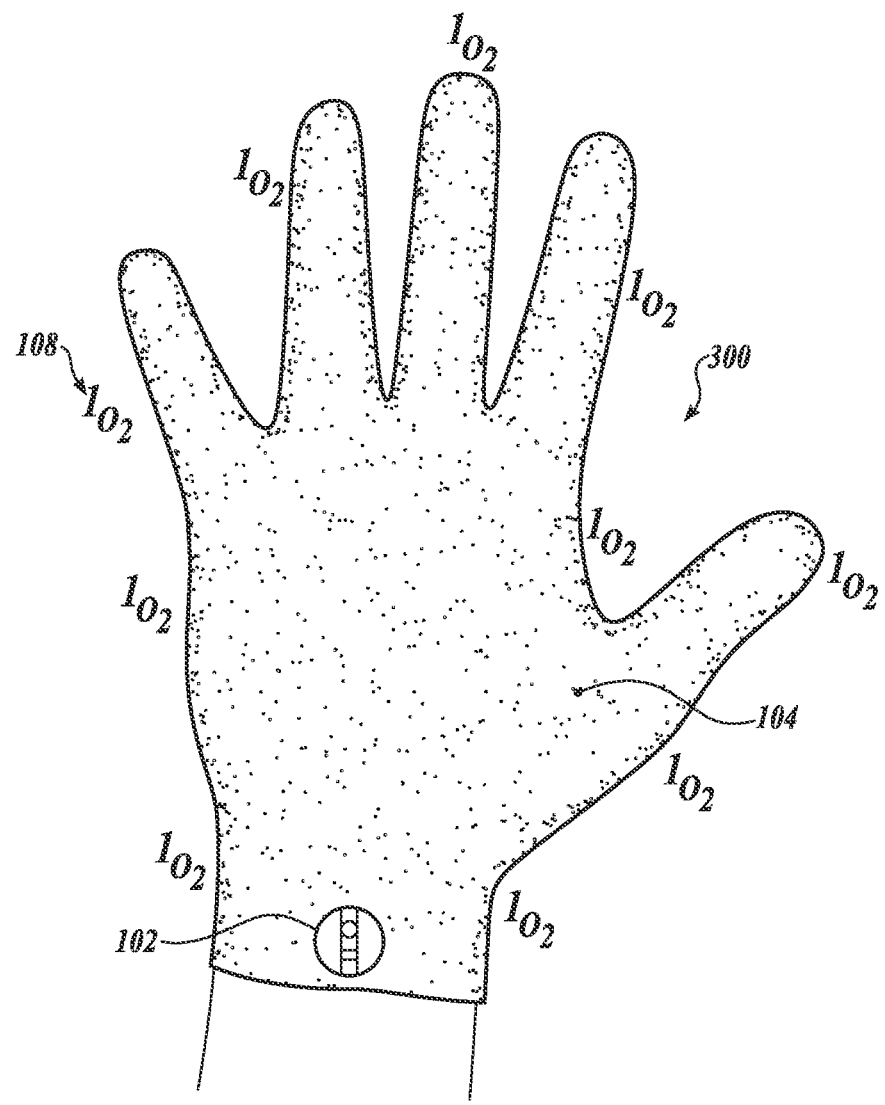
FIG. 3 is a diagrammatical illustration of a glove in accordance with one embodiment.
Figure 4:
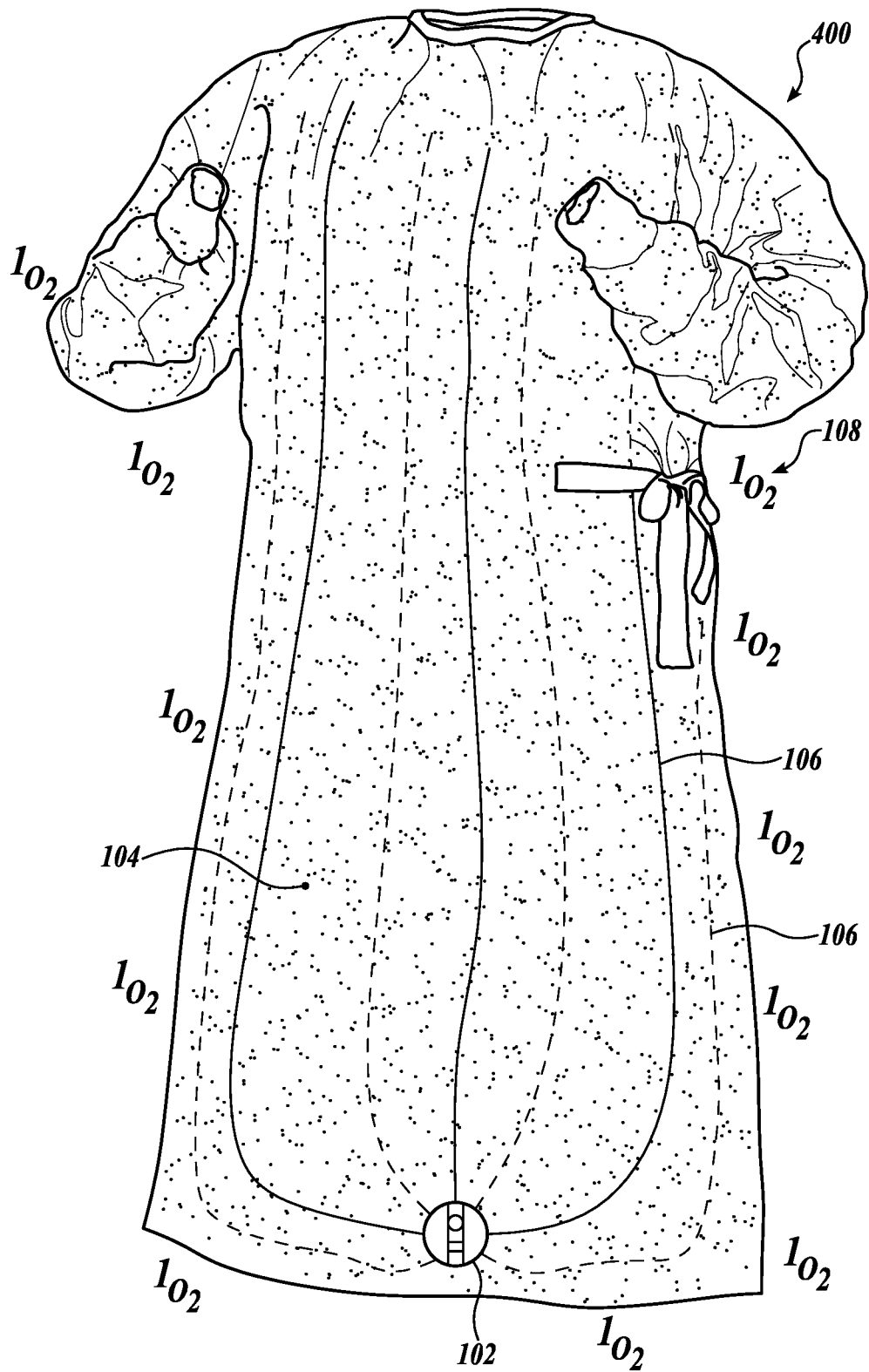
FIG. 4 is a diagrammatical illustration of a gown in accordance with one embodiment.

Referring to FIGS. 2, 3, and 4, one or more one optical fiber 106 which emits light along the length of the fiber are woven into the interior or bonded to the exterior surface of the material of the mask or respirator 200, glove 300, gown 400, or other PPE that is impregnated with the photosensitizer 104. The optical fiber 106 is connected to or butts against the LED 102 such that light is conducted throughout the surface and internal substance of the material to be disinfected. The optical fiber 106 can be referred to as an edge-emitting or side-emitting light fiber. That is, the optical fiber 106 has less than total internal reflection, and the light carried by the optical fiber 106 will radiate along the length of the fiber 106.

Figure 5:
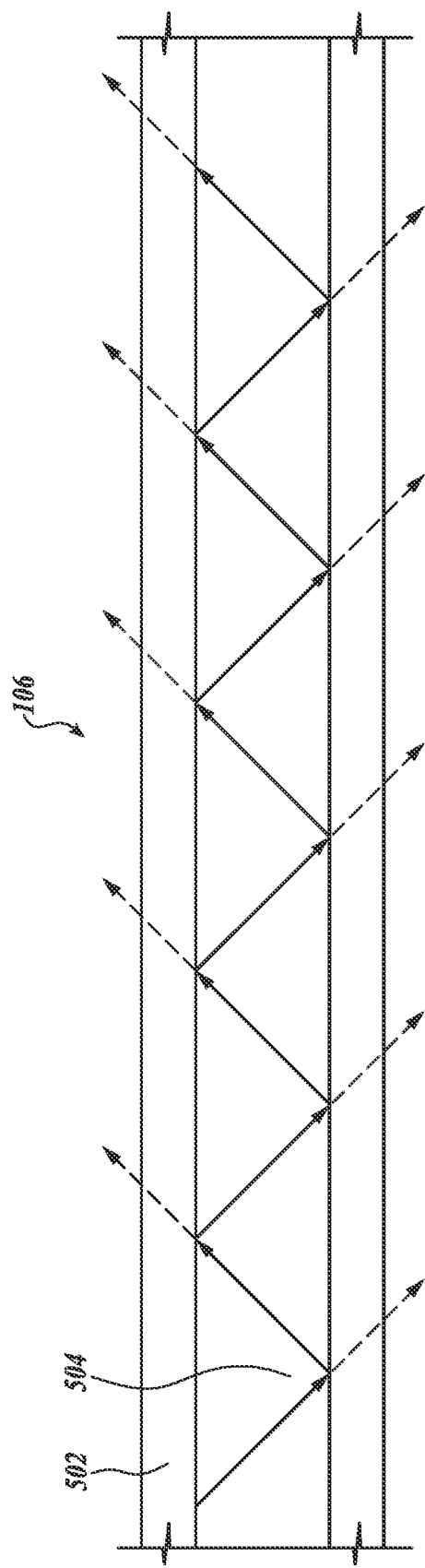
FIG. 5 is a diagrammatical illustration of an edge-emitting light fiber.

Referring to FIG. 5, a schematic illustration of an edge-emitting optical fiber 106 shows a center core 504 and a cladding or sheathing 502 surrounding the center core 504. The optical properties of the sheathing 502 provide reflection of some of the light back through the center core 504 and transmittance of some of the light through the edge sheathing 502 to the exterior. Thus, the optical fiber 106 will radiate light along the length of the optical fiber 106.

Further, the optical fiber 106 can also be selected to have certain light transmission properties to carry a certain wavelength of light. By selecting an optical fiber 106 having certain properties, the light impinging on the photosensitizer 104 can be optimized for the peak absorption waveband of the photosensitizer 104.

Referring to FIG. 2, one or more LED light 102 abuts at least one optical fiber 106 which emits or leaks light along its length. At least one LED 102 with optical fiber 106 is positioned externally, but in direct contact across the mask 200 surface and length in order to leak light and provide illumination across the entire mask surface. Optical fibers 106 are flexible and can conform to the curved surfaces on both sides of the mask 200. Edge-emitting optical fibers 106 can provide light to areas impregnated with photosensitizer 104 even when material is folded over. In one example, at least one LED light 102 can be clipped to at least one of the edges of the mask 200, providing continuous or intermittent illumination for one or both mask surfaces. An optical fiber 106 can also be incorporated into the straps of the mask 200 to disinfect greater surfaces of the mask 200.

Referring to FIG. 4, one or more LED 102 is abutted to one or more one edge-emitting optical fiber 106, but preferably to a plurality of optical fibers 106 arranged into a pattern which provides for illumination of substantially the entire surface of the front of the gown 400. The edge-emitting optical fibers 106 can be deployed only in the areas of the material impregnated with the photosensitizer 104. In one example, the edge-emitting optical fibers 106 are positioned generally parallel to each other. However, any pattern of arranging the edge-emitting optical fibers 106 to illuminate as much of the area of the gown 400 that is impregnated with the photosensitizer 104 can be used, such as a crossing pattern or a combination of parallel and crossing patterns.

In examples, edge-emitting optical fibers 106 can be placed on the exterior surface of the material, on the interior surface of the material, or embedded in the material. The edge-emitting optical fibers 106 can be used in the areas of the material intended to be impregnated with the photosensitizer 104. The use of edge-emitting optical fibers 106 can provide consistent illumination over substantially the entire area of material that is impregnated with the one or more photosensitizer.

FIGS. 1 and 3, show respectively a mask 100 and glove 300 without optical fibers. In these examples, the LED 102 can have a lens to emit light in a forward direction across the mask or glove surface in a continuous or intermittent fashion.

In FIG. 3 at least one clip-on LED 102 is attached to the proximal portion a glove 300, providing illumination for the glove surface. A lens can direct the light from the LED 103 distally toward the palm and the fingers with a directional lens. The light will then impinge on the material impregnated or applied with the photosensitizer 104.

In an example, the masks 100, 200, glove 200, gown 400, or other PPE can be comprised of an optically transparent polypropylene, polystyrene, polycarbonate, polyethylene, or polyester material which can transmit light. In this example, at least one light source 102, such as an LED may provide adequate illumination without an optical fiber 106, though use of at least one optical fiber is not precluded in any way.

In an example, a 3-D printer can be used to manufacture masks or respirators 100, 200, gloves 300, gowns 400, and other PPE, incorporating at least one photosensitizer 104. The optical fibers 106 can optionally be printed into the material as well. The optical fibers 106 incorporated into the material enable light penetration and delivery throughout substantially the entire material impregnated with the photosensitizer of the mask or respirator, glove, gown, or personal protective equipment. A 3-D printer may also be used to print electroluminescent wires into the material, which when powered by a battery, emit light.

An advantage of the use of optical fibers 106 embedded within or bonded to the surface of mask or respirators 100, 200, glove, 300, gown 400, or other PPE material is that thicker material can be used, which may afford more protection and enable the useful life of the mask, respirator, glove, gown or PPE to be extended well beyond a single day or normal shift use. Though white light can be used for illumination of photosensitizers, lights emitting specific wavebands or wavelengths absorbed specifically by the photosensitizer 104 may result in a more efficient use of photosensitizer and light energy to achieve photodynamic action. Thereby, requiring a lower photosensitizer concentration for disinfecting photodynamic action.

In an example, light from the light source 102, optionally from at least one LED, is of a waveband or wavelength that matches the peak absorption spectra of the photosensitizer 104 to be used for disinfection. For example, methylene blue absorbs light best in the yellow and especially in the red wavebands, and the at least one LED 102 that emits in the red and/or yellow spectrum can be incorporated into the article of PPE. Methylene blue has a peak absorption band around 664 nanometers which is red light, erythrosine has a peak absorption band of around 530 nanometers which is green light, and riboflavin can absorb light in the blue waveband around 470 nanometers. However, a photosensitizer is possible to absorb light of different wavebands. The absorption spectra of photosensitizers can be determined experimentally or may be published in literature.

In an example, the mask or respirator 100, 200, glove 300, gown 400 and other PPE incorporates a polymeric reservoir that contains a photosensitizer solution, that elutes the photosensitizer solution into the material over time and at a rate that permits renewal of an effective concentration and dose of photosensitizer 104. In this example, photobleaching of the photosensitizer which renders it inactive is counteracted by constant renewal of fresh photosensitizer solution permeating the mask or respirator 100, 200, glove 300, gown 400, or other PPE. The polymeric reservoir can be constructed from an opaque polymer or plastic substance in order to prevent inadvertent light exposure to photosensitizer solution within the reservoir, which can induce photobleaching, which is the auto-destruction of photosensitizer molecules by singlet oxygen generated from light exposure.

In an example, indoor light exposure on a mask, glove or gown or other personal protective equipment surface with previously or newly applied photosensitizer may provide for a continual photodynamic disinfection effect against contaminating viruses, bacteria, and/or fungi in the ambient environment which adheres to the mask, gown, or other personal protection equipment in combination with the built in light source.

Figure 6:
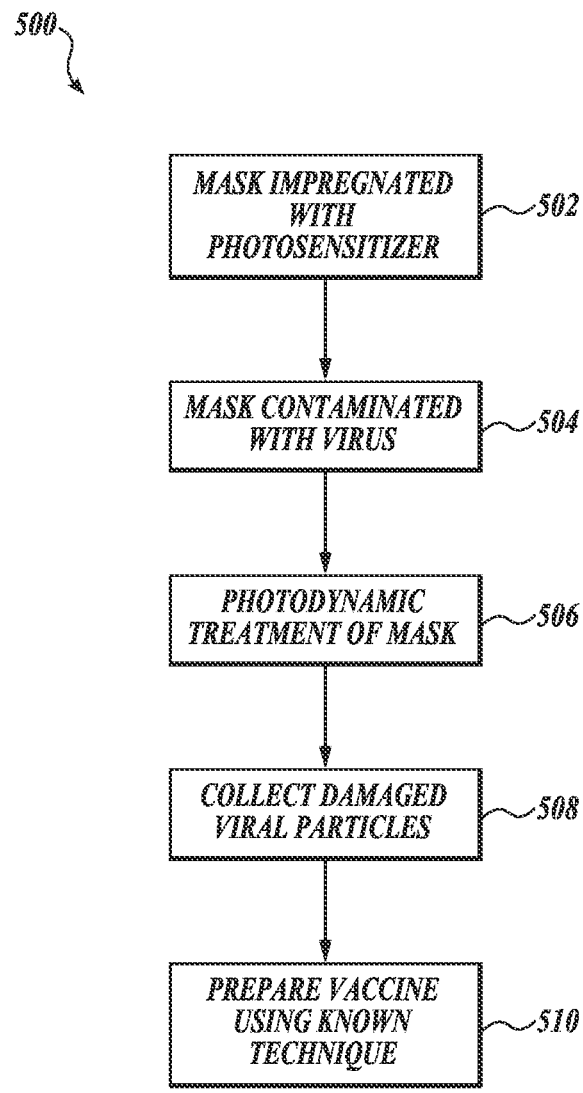
FIG. 6 is a flow diagram of a method of making a vaccine in accordance with one embodiment.

Referring to FIG. 6, a method for creating a vaccine is diagrammed. The method of FIG. 6 describes the use of a contaminated mask; however, any other article that is photodynamically treated may be used.

In one example of a method, after light and photodynamic treatment, virions or other pathogenic microorganisms present on a mask which have been rendered non-infective may serve as a vaccine source for immunogens. For example, damaged, inactivated non-infectious virion and viral fragments retained on a treated mask surface, when worn by the user, may enter the oral cavity, nasal passages, nasopharynx, or upper and lower respiratory tract and lead to a beneficial immunization effect specific to the contaminating virus or other microbe population. This unexpected benefit can be optionally augmented and enhanced by administration of known immunologic adjuvants such as aluminum salts, squalene, saponins, Freund's adjuvant, monophosphoryl lipid A, AS04, Endocine™, or other known or contemplated vaccine adjuvants, applied to the oral and/or nasal mucosa, or administered subcutaneously, intramuscularly, or by other routes. Another unexpected benefit is the inducement of a localized immune response driven by immune cells in the skin which generate an immune response against virus or other pathogens which adhere to the face.

Referring to FIG. 6, an example vaccine production method includes the following steps. In step 502, a mask, such as 100 or 200, impregnated with a photosensitizer 104 is prepared. In step 504, the mask 100 or 200 is contaminated with a virus, such as the SARS-CoV-2. In step 506, after contamination with the virus, photodynamic treatment of the mask is performed using any artificial light source or natural light as described herein. In step 508, the damaged viral particles are collected from the mask surface using at least one swab or polymeric or cloth wipe material. Alternatively, damaged viral particles are harvested by placing segments of the mask in a saline solution. In step 510, the damaged viral particles are collected, isolated, and used to manufacture a vaccine using known, well developed techniques.

The vaccine created in the example of FIG. 6 can be tested using preclinical techniques well known in the virology laboratory for antibody generation against the virus. The vaccine with or without vaccine adjuvants is tested clinically as is known in the art, for example, starting with healthy volunteers in a phase 1 type study and then followed by testing as a preventative, and a therapeutic agent.

Figure 7:
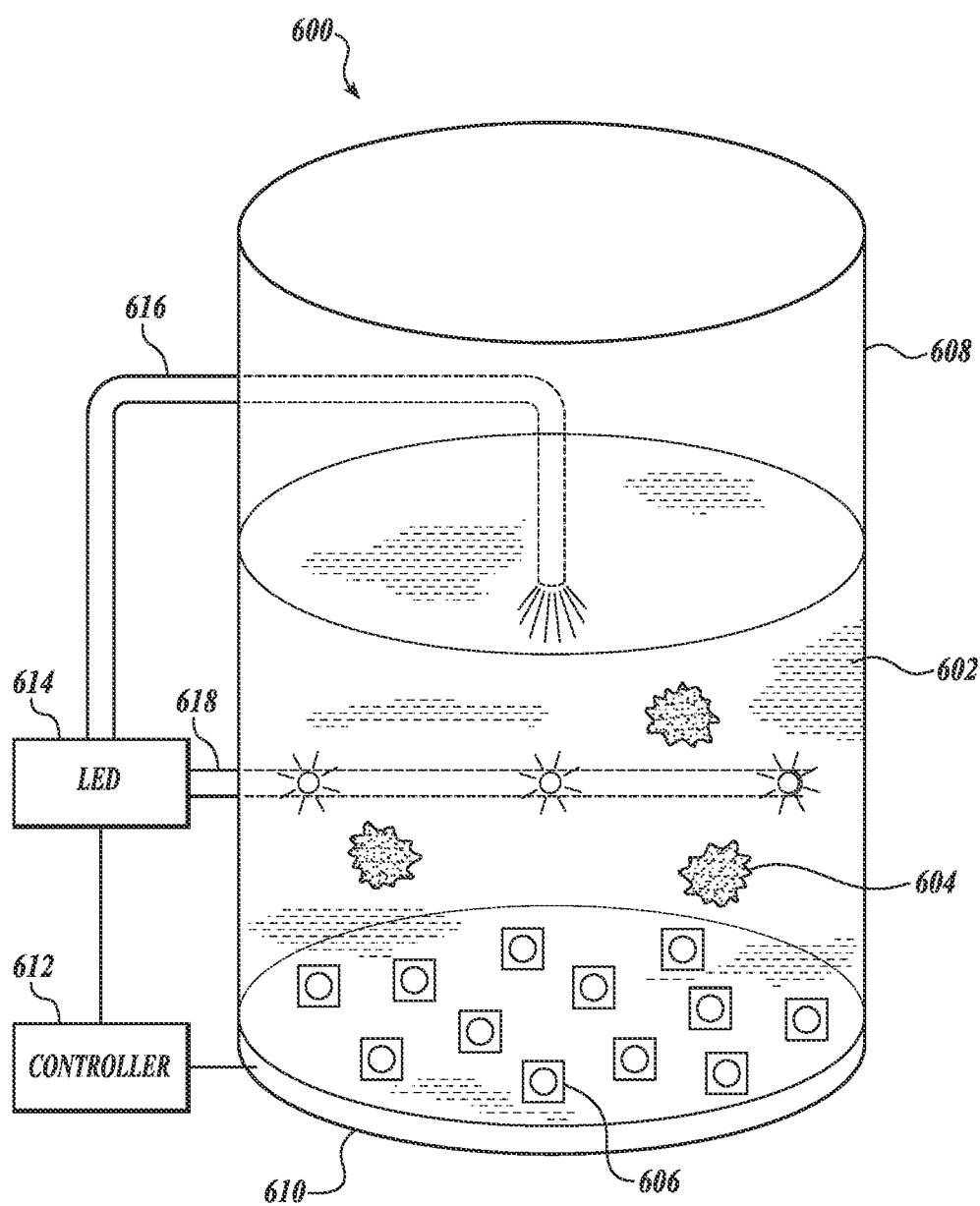
FIG. 7 is a diagrammatical illustration of a photodynamic reactor system in accordance with one embodiment.

Referring to FIG. 7, an example of a photodynamic reactor system 600 is illustrated. The photodynamic reactor system 600 can be used for the testing and evaluation of photosensitizers to different wavebands, different light fluence rates, and different illumination times. In addition, the photodynamic reactor system 600 can be used for the production of a vaccine. The photodynamic reactor system 600 can be used to photodynamically treat microbes, viruses, etc. The photodynamic reactor system 600 can be installed, for example, in a suitable biosafety viral laboratory or vaccine manufacturing facility capable of safely handling live pathogens and viruses.

The reactor system 600 includes a reactor vessel 608. The reactor vessel 608 can be constructed from a nonreactive metal, such as stainless steel, or a polymer or a plastic which is leak-proof and opaque to light. The reactor vessel 608 can incorporate a built-in light source 610, preferably but not exclusively comprised of one or more LEDs 606 or other light sources. The light source 610 can be placed on the bottom of the vessel 608. The LEDs 606 can be arranged on the bottom over an area generally matching the size of the vessel diameter. The LEDs 606 are configured to radiate light upwards into the interior of the reactor vessel 608 so that essentially the entire contents of the reactor vessel are irradiated with the light from the LEDs 606.

In addition to or as an alternative to the LED array 610, in one example, light is delivered by an external or internal bank of LEDs or at least one laser which lines the container or vessel 608. In this manner, light is delivered more uniformly to the virus 604 or other pathogen present in the photosensitizer solution 602.

Alternatively, or in addition to the external array, one or more optical fiber 616 and 618 are connected to at least one LED 614 or laser for conveying light to the solution 602 internally. The optical fiber 616 can be positioned in the central portion of the reactor vessel 608, while the optical fiber or fibers 618 convey light radially inward from the inside walls of the reactor vessel 608. However, other arrangements of lights and optical fibers can be configured in any manner to achieve optimal light exposure and a proper photodynamic effect which inactivates the virus or pathogen.

The lights 606 and 614 can be adjustable in intensity (i.e., fluence rate), time of illumination, and waveband. The lights 606 and 614 can be controlled using the controller 612. Controller 612 can include a processor, a memory, and a user interface. The user interface, such as keyboard, mouse, touchscreen, and the like, can be used to program one or more of the adjustable parameters of the lights 606 and 614. Lights 606 and 614 can also be programmed to be emitted in pulses, continuously, or as an increasing intensity ramping mode. The wavelength or waveband of lights 606 and 614 can be varied by incorporating light sources such as LEDs or lasers of different emission wavelengths and wavebands (e.g. RGB LEDs). Light intensity can be varied through known circuitry and control systems.

In an example, the testing process can be automated. The testing parameters can be stored in the controller's 612 memory such that preprogrammed light dosimetry is enabled for rapid testing, which includes the option of adding varying concentrations of photosensitizer solution, varying viral concentrations and cells containing live virus to one or more of the reactor vessels. Alternatively, the interior of a single reactor vessel can be divided into compartments. The controller's 612 memory can also store data for use in setting the testing parameters. For example, the controller's 612 memory can store a database of photosensitizers, previous conditions tested, and the results. The controller's 612 memory can also store a database of photosensitizers and the peak absorption waveband of each photosensitizer. The controller 612 can refer to the stored data to control the lights 606, 614 to emit the peak absorption waveband of the photosensitizer.

In preparing for photodynamic treatment, the interior of the reactor vessel 608 is sterilized optionally using ultraviolet light or other known disinfecting agents. The reactor vessel 608 is then filled with a photosensitizer solution 602. The photosensitizer solution 602 can contain one or more photosensitizer and can include saline or any other biocompatible solution. The photosensitizer solution 602 can be spiked with live virus 604 or other pathogenic microorganisms, then exposed to light of the proper wavelength or waveband.

After exposure to different fluence rates and total doses of light, different wavebands, and different photosensitizers at different concentrations, the photodynamically treated virus is harvested from the reactor vessel 608, the virus is isolated, and purified for testing of viability and infectivity using standardized viral assays. Once the correct range of test conditions of photosensitizer and light dosimetry are evaluated and confirmed that disinfect virus or pathogens, the inactivated virus or pathogen is recovered from the reactor vessel 608 and processed into a vaccine for preclinical and clinical testing. To facilitate more rapid testing, reactor vessels of different sizes, shapes, materials, can be constructed such that varying amounts of photosensitizer can be added to isolated compartments which enables rapid testing of different photosensitizers, different concentrations, different light parameters, and the like.

In an example, once an effective photosensitizer concentration and light dose is determined, the effective photosensitizer and light parameters can be used to treat articles, including the personal protective equipment, or other articles, or for any method of disinfection.

In an example, once an effective photosensitizer and light dose is determined, the process can be scaled up using banks of vessels and containers of significant volume in order to facilitate rapid manufacture of vaccine.

Figure 8:
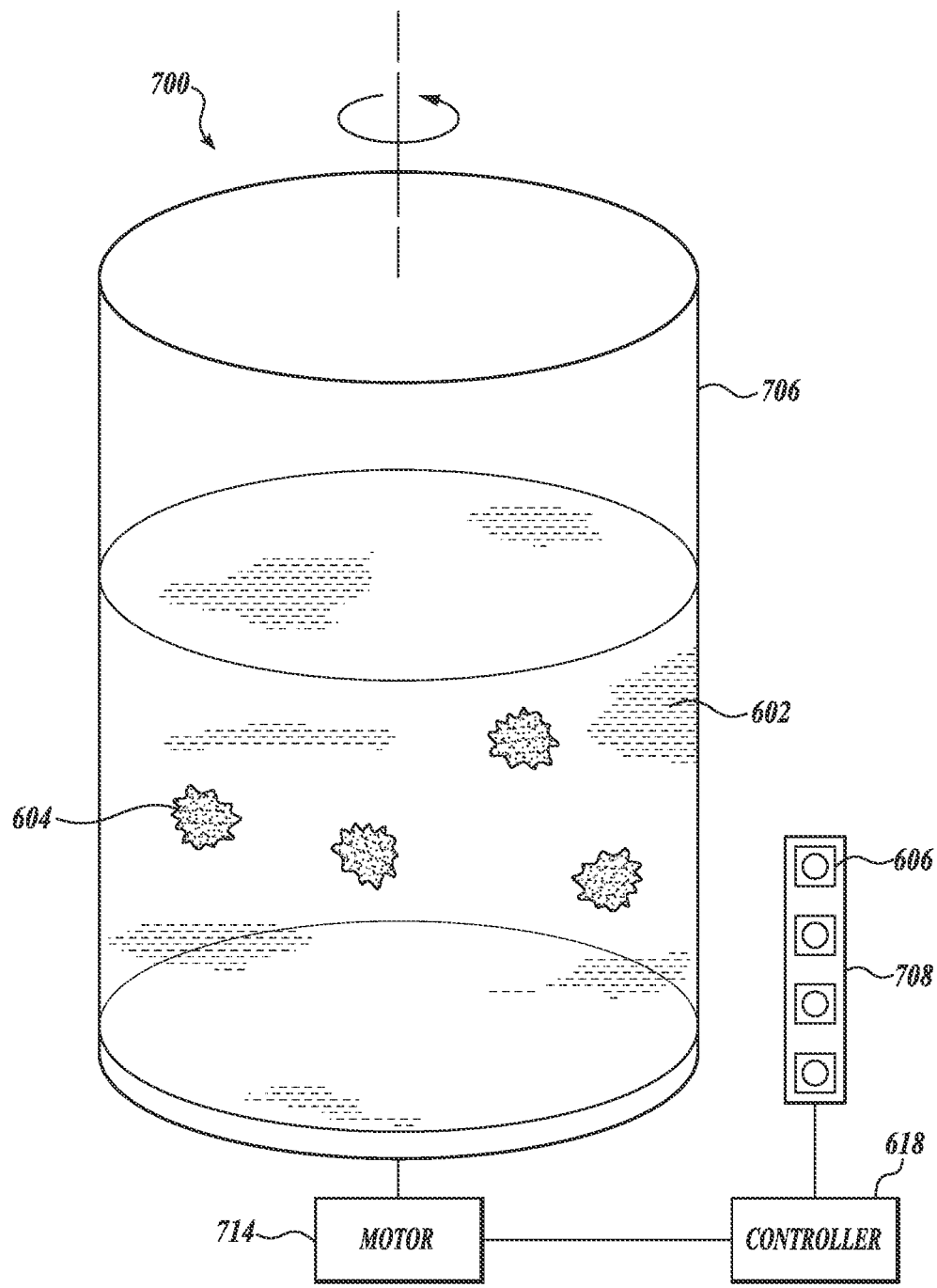
FIG. 8 is a diagrammatical illustration of a photodynamic reactor system in accordance with one embodiment.

FIG. 8 is a schematic illustration of another example of a photodynamic reactor system 700. The photodynamic reactor system 700 is for photodynamically treating microbes, viruses, and other pathogens similarly to the photodynamic reactor system 600. FIG. 8 uses like numbers to represent similar parts, the differences between the two systems are described below.

In an example, the photodynamic reactor system 700 includes a reactor vessel 706 that has walls constructed from an optically clear polymer, glass, or plastic. An external light source 708 is placed adjacent to the exterior wall of the reactor vessel 706, such that the light emitted from the external light source 708 penetrates the wall of the reactor vessel 706 and illuminates the contents on the interior of the reactor vessel 706. In an example, the external light source includes LEDs 606 that can be adjusted in intensity (i.e., fluence rate), time of illumination, and waveband, as described above. The external light source 708 is controlled by the controller 618 as described above. In an example, the external light source 708 is stationary and illuminates the photosensitizer solution 602 on one side of the reactor vessel 706. In an example, the reactor vessel 706 is spun or rotated or otherwise moved by a motor 714 such that the photosensitizer solution 602 spiked with virus 604 or other pathogens is exposed to light from an external light source 708 in a uniform manner. The external light source 708 is adjustable in intensity (i.e., fluence rate), time of illumination, and waveband using the controller 618. Further, the controller 618 can be used to deliver light in pulses, continuously, or as an increasing intensity ramping mode. The wavelength or waveband can be varied by incorporating light sources such as LEDs or lasers of different emission wavelengths and wavebands (e.g. RGB LEDs). In an example, the process can be automated such that preprogramed light dosimetry is enabled for rapid testing, which includes the option of adding varying concentrations of photosensitizer solution, varying viral concentrations and cells containing live virus.

In both embodiments of FIG. 7 and FIG. 8, after performing photodynamic treatment, the photodynamically treated virus 604 and 704 or other pathogen can be transferred using a pipe, tube, or other conduit into a processing device which filters out any residual photosensitizer and photo-byproducts, and then purifies the solution for manufacturing of the vaccine using known processes in an automated fashion.

In other examples, applicators are disclosed for applying photosensitizers to articles. Applicators can include, for example, brushes, rollers, sprayers or mist producing applicators. Applicators can apply photosensitizers as a liquid, gel, or powdered composition. The disclosed applicators are used to swab, brush, paint, spray, mist, or otherwise apply the photosensitizer 104 on articles including, but not limited to, the PPE articles, clothing, such as hats, gloves, shoes, socks, and other apparel worn by a person in order to provide for a disinfecting procedure. The applicators can also be used for applying photosensitizers to hard surfaces, such as furniture, equipment, walls, floors, or any other surface.

Photosensitizer compositions may also include excipients, such as scents, for example, citrus, lavender, bergamot, orange blossom, chamomile, sage, eucalyptus, lemon and the like. The concentrations of excipients can range from 0.01% to 10.0% by weight in solution, and powders such as apple fragrance, banana fragrance, rose, bergamot, cherry, citrus, lavender, in concentrations can range from 1 mg to 10 gm/L.

Referring to FIG. 9, an applicator 800 for applying a composition containing at least one photosensitizer is illustrated. The applicator 800 includes a hollow polymeric handle 802 and an absorbent material 804, such as a foam sponge 804, attached to the distal end of the handle 802. Although a sponge 804 is used in the illustrated embodiment, the applicator 800 can be made with other types of absorbent materials. In an example, the absorbent material can be a formed on the exterior of a roller. In some examples, a roller can use foam or fibrous materials. Other examples of absorbent materials used in the applicator 800 may include natural and synthetic bristles formed into a brush.

The interior of the hollow handle 802 can be filled with a solution or gel 806 containing at least one photosensitizer. The photosensitizing solution 806 diffuses into the foam sponge 804 which when gently pressed on an article, such as a public mask outer surface leaves a thin film of photosensitizer on the mask outer surface.

In an example, the hollow polymeric handle 802 is made from a material opaque to visible and ultraviolet light which prevents photobleaching (auto-destruction of a photosensitizer by singlet oxygen attacking the photosensitizer molecules instead of viral particles) of the contained photosensitizing solution or gel 806.

In an example, the photosensitizers in the solution or gel 806 include methylene blue, erythrosine, and riboflavin in equal molar concentrations, and in equal volumes. Methylene blue which is used medically, food grade erythrosine also known as FD & C Red No. 3, and food grade riboflavin which is vitamin B2 are used due for safety reasons when used by persons constituting the general public, and when used around children. Methylene blue, erythrosine, and riboflavin at the concentrations contemplated are generally non-toxic even when ingested accidentally, or inadvertently applied to the skin.

In an example, the photosensitizers in the solution or gel 806 include methylene blue, erythrosine, and riboflavin in different molar concentrations ranging from 0.01 µM to 1,000 µM.

In an example, a gel with one or more photosensitizer for use in the applicator 800 is prepared using substances, such as commercially available ultrasound coupling gels and gelling agents. In an example, a "gel" has the International Union of Pure and Applied Chemistry (IUPAC) meaning of any "non-fluid colloidal network or polymer network that is expanded throughout its volume by a fluid." In an example, a "gel" can be a semi-solid. In an example, a "gel" can be a composition including a gelling agent. The gelling agent or agents can include food grade gelling agents, such as agar which can be extracted from seaweed, pectins which can be extracted from apples and oranges, carrageenan which can be extracted from seaweed, guar gum which can be extracted from the Indian guar plant, locust bean gum which can be extracted from carob seed, and gelatins which are produced from animal derived collagens. Other emulsifying agents and thickeners could also be used in the gel including, but not limited to, hydroxyethyl cellulose, liposomes, cellulose, and the like. For photosensitizer gel compositions, the concentration of each gelling agent, each emulsifying agent, and each thickener can range from 1% to 40% by weight in one example, or 1% to 40% by volume in one example.

In an example, the gel 806 is adjusted such that easy flow of the gel 806 is enabled into the foam sponge 804. The applicator 800 allows photosensitizers to be applied to any article desired to be inactivated of microbes, viruses, and pathogens.

The gel 806 with one or more photosensitizer can be applied to any article, such as clothing and personal protective equipment. The applicator 800 allows application of the gel 806 onto surfaces of the articles. In one example, the applicator 800 can be used to apply the gel 806 to the surface of N95 type of respirators typically used in the medical setting. The photosensitizing gel 806 improves the ability of the gel to coat a hydrophobic surface, such as is commonly found on the outward facing surface of surgical masks and N95 type respirators. In an example, a hydrophobic surface on a mask or other article is made from a polypropylene sheet. However, other known hydrophobic surfaces may also be coated with the gel 806 for improved application.

In examples, the sponge 804 material can be chosen from naturally occurring sea sponge organisms typically used for cleaning and wiping, or from synthetic sponge material usually composed of hemp fiber, wood pulp, and sodium sulfate. Other synthetic sponge materials are manufactured from polyesters.

Laboratory testing using known methodologies can be used to determine suitable sponge materials that elute the photosensitizing solution or gel 806 most effectively onto the articles, including hydrophobic and hydrophilic public facemask and N95 type mask surfaces. An effective eluting procedure can leave an even thin film that does not bead up. The application of photosensitizer can be confined to the outer surface of the public facemask and N95 type respirator which faces outwards when worn by a user. All outer surfaces of the public facemask, and N95 type respirator, including the ear straps or loops can be coated with the photosensitizer solution or gel 806.

In examples, the hollow handle 802 can be provided in different shapes, sizes, and configurations, capable of containing various volumes of photosensitizing solution or gel 806. Additionally, the hollow handle 802 can be refillable. The hollow handle 802 can be provided with ergonomic characteristics with respect to the shape and volume of the handle to enhance flow characteristics of the photosensitizing solution or gel 806, ease of refill, and lack of leakage from the sponge 804.

In an example, the thickness, shape, size, and porosity of the sponge 804 can be tested for suitability aimed at maximizing photosensitizing solution or gel 806 deposition speed for ease of application to all types of materials and surfaces, all types of face coverings and face masks, face shields, head coverings, shoe covers, netting type of materials, garments and clothing, shoes and other footwear, and the like.

In an example, the applicator 800 is used for a one time photosensitizer application to a potentially virus contaminated N95 type respirator used in a medical setting by a healthcare worker and then disposed of. Using a new applicator 800 for each N95 type respirator obviates the risk of transfer of live virus to a second mask.

In an example, for single use disposable situations, the handle 806 can be solid, and the sponge 804 can be manufactured with pre-loaded photosensitizing solution or gel 806. In the reduced risk environment (when compared to a high risk hospital setting for example) where public facemasks are used, the applicator 800 can be effectively used on multiple public facemasks if required due to much lower virus transmission.

In an example, a light source 812, such as a light emitting diode connected to a battery can be incorporated into the handle 802 in order to provide a bright light for dim light conditions. The light source 812 can be activated during the photosensitizer application process, and be positioned after the application process such that light is emitted onto the surface. In an example, the light source 812 can be adjustable in intensity (i.e., fluence rate), time of illumination, and waveband.

In an example, a security cap 808 provides a waterproof, leakproof cover in which the sponge 804 is placed in order to prevent leaking and loss of photosensitizing solution or gel 806. The cap 808 can be made to fit tightly enough to prevent accidental dislodgement or unwanted uncovering of the sponge 804 by young children and toddlers. The incorporation of the child-proof cap 808, and the containment of the photosensitizing solution or gel 806 within the handle 802 are measures that reduce risk of accidental ingestion of the photosensitizing solution or gel 806. An added safety factor is the use of food grade and medical grade photosensitizers and food grade gelling substances in the unlikely scenario of accidental ingestion by a toddler or a child.

Further, containing one or more photosensitizer in a gel formulation, such as in the handle 802, reduces the risk of spillage of the photosensitizers as compared to an aqueous solution which can stain, damage, or degrade materials and surfaces not intended to be disinfected, such as flooring, carpeting, countertops, sinks, furniture, or other household items and objects. However, both a photosensitizing gel or a photosensitizing solution can be used with the applicator 800, and there may be applications where a gel is advantageous and applications where a solution will be advantageous.

Referring to FIG. 10, a second embodiment of an applicator 1000 is illustrated. The applicator 1000 includes a bottle 1008 that can be pressurized by the use of a manually actuated pump 1004. The applicator 1000 includes a finger trigger 1006 that opens a valve such that the pressure within the bottle 1008 propels a photosensitizing solution within the bottle out through a nozzle 1002. The nozzle 1002 may have a wide angle fan spray pattern or a conical spray pattern. The nozzle 1002 may be adjusted to change the spray pattern, such as by rotating the nozzle 1002. Various nozzle spray pattern designs can be tested for use with the spray bottle applicator 1000. The testing of various nozzle configurations producing various droplet sizes and application pressures is performed in order to apply an adequate virucidal photosensitizer layer to the outer public mask surface, that does not leak through to the inner surface of the public mask, where unwanted contact to the skin, nose, nostrils, lips, mouth or mucous membranes of the nasal passage and mouth may occur.

Referring to FIG. 11, an illustration of a mask 1100 is shown as a representative article incorporating a photosensitizer solution or gel 806 which has been applied by an applicator as described above. In an embodiment, an indicator 1104 can be attached on the mask 1100 or on any articles that have been treated with the photosensitizer solution or gel 806. The indicator 1104 provides a user with a notification that the photosensitizing solution or gel 806 should be reapplied on the article. In an example, the indicator 1104 is provided as a removable stick-on tape incorporating methylene blue or another photosensitizer, which when photobleached by ambient light, will change from a readily visible blue color to a colorless condition. Such indicator 1104 can be based on the photobleaching principle. The colorless condition is produced when light activated methylene blue is destroyed by singlet oxygen yielding a colorless molecule no longer capable of generating virucidal singlet oxygen. At that point, the user may reapply another coating of the photosensitizer solution or gel 806 for continued viral decontamination.

In an example, the facemask 1100 or other face covering can be more securely adhered to the facial surface to reduce air leaks around the mask edges by using, for example, a non-irritating skin adhesive liquid formulation, such as Mastisol™, Turbot Skin Tac™, Jobst It Stays™ body adhesive, or thin width double sided skin adhesive tape such as Vapon Topstick® or Fearless Tape. Reduction of the air leak can prevent viral transmission to the user when virus laden droplets are present in the inhaled air.

Example 1

A 1 micromolar methylene blue (MB) stock solution can be created using medical grade saline as the diluent. The MB solution is applied onto mask component surfaces and a red light emitting LED is incorporated into the lateral edge of the mask and activated. Both surfaces of the mask are simultaneously illuminated. As the mask is worn by the health care worker (HCW), and the HCW continues to care for infected patients, the photosensitizer coated mask comes in contact with the pathogen which may be airborne. Adherent viruses, bacteria, and/or fungi are continually inactivated by the continuous generation of singlet oxygen due to the photodynamic process and reciprocity principle known in the photodynamic therapy art, whereby effective microbial or viral inactivation occurs even at light levels lower than those used for the initial disinfection, due to the prolonged light exposure. The inactivated viral particles or other non-infectious microbial components generated by singlet oxygen damage enter the oral cavity or nasal passages and can lead to a vaccine-like immune response against the pathogen, which is optionally augmented by a intranasally applied adjuvant such as Endocine™.

Example 2

A sequence of disinfection experiments can be performed in an appropriate laboratory setting using differing photosensitizers in a variety of available gel and liquid formulations, which may optionally contain alcohols or other beneficial substances in addition to at least one photosensitizer. Living viral, bacterial, or fungal specimens are inoculated onto various materials used in the manufacture of mask, gowns, and other personal protective equipment, followed to systematic light exposure entailing different fluence rates, illumination times, illumination patterns, wavelengths, and wavebands, followed by viral viability assays, in order to optimize the disinfection process in terms of time, space, and resources.

Example 3

At least one of a small plastic reservoir with a narrow opening tip can be attached to a N95 respirator, enabling elution of a steady amount of photosensitizer solution into the mask material. The mask material permits diffusion of the photosensitizer solution throughout the material which enables effective photoactivation by light, enabling continued effective disinfection by constant renewal of the photosensitizer which otherwise undergoes photobleaching in a time and light intensity dependent manner, which ends the photoactivation process. The N95 mask can also incorporate at least one LED on each edge of the mask, powered by a battery worn behind each ear. The dual LED array illuminates both sides of the mask due to a forward emitting lens on the LED aimed towards the mask center.

Example 4

A mask, N95 respirator, or gown contaminated with virus or other pathogens is swabbed or cut into pieces after photodynamic treatment with applied or incorporated photosensitizer and light exposure using multiple light and photosensitizer dosimetry parameters for processing to test viral or pathogen viability. When the proper photodynamic parameters that disinfect the virus or other pathogen are determined, the photodynamic parameters are duplicated, made into a photosensitizer composition to be applied using an applicator.

Example 5

After photodynamic treatment of a mask contaminated with a virus, such as the SARS-CoV-2, an experiment can be performed using damaged viral particles collected off a mask surface using at least one swab or polymeric or cloth wipe material. Alternatively, damaged viral particles are harvested by placing segments of the mask in a saline solution. The damaged viral particles are collected, isolated, and used to manufacture a vaccine using known, well developed techniques. The vaccine can be tested with adjuvants in preclinical and clinical settings using developed testing techniques and established protocols for photodynamically generated antigenicity of damaged virus or other pathogens. It is understood that virus be completely inactivated or be attenuated as in live virus vaccines by the photodynamic treatment.

Example 6

A virally exposed photodynamically treated surgical mask can be inverted and reused which exposes the HCW mouth and nose to an increased concentration of viral antigens which are immunogenic systemically, and locally on the face surface, which reduces transmission risk from facial pathogen contamination.

Example 7

A person desirous of entering a hospital or clinic from the outside can be provided with a swab, brush, roller, or mist producing device which enables application of photosensitizer to the entire apparel surface, including shoes, socks, and the sole of the shoes or other footwear. Subsequent delivery of photoactivating light is delivered from an external source, outside or just inside the hospital building, medical clinic, house, or other indoor setting, or just prior to boarding a cruise ship, airplane, or other conveyance where viral or other pathogen transmission is possible by a person unknowingly contaminated by virus or other pathogen.

Example 8

In a series of laboratory experiments, various combinations of photosensitizers, at varying concentrations and volumes can be tested for virucidal activity. One set of experiments utilizes food grade riboflavin, medical grade methylene blue, and food grade erythrosine in equal or varying volume parts and at equal or varying molar concentrations. The formulations which can provide for virucidal activity, which is defined as at least a 4-log viral titer reduction, are selected for use in applications, such as clothing and personal protective equipment. Further laboratory testing can be used to determine suitable gel formulations which may utilize food grade gelling agents such as agar, pectins, carrageenan, guar gum, locust bean gum, or gelatins, or combinations of these food grade gelling agents. An example gel formulation is one that can be contained within a hollow handle which flows into a distal sponge easily and is evenly applied to public facemask surfaces using the handheld applicator in a simple one-direction wiping motion.

Example 9

A photosensitizing solution which may be aqueous or gel can be developed and tested as a spray to be suitable for application to fabrics, clothing, headwear, footwear, and other protective garments, gowns, face coverings, gloves, and the like. The spray application covers a large surface area quickly and easily, and the photosensitizer solution or gel provides for improved photosensitizer adherence to the fabric or various coverings and garments and causes rapid spray droplet settling onto the surface to be disinfected, which negates inhalation risk and skin and eye exposure. The photosensitizing gel can be applied to a head covering such as a hat or baseball cap, a public mask, normal clothing, a gown, and shoe surfaces, of a worker prior to entering a place of employment, or when using public transportation, for users in a school setting, when in an eating and drinking establishment, attending a social or music event, in a crowded meeting venue, at a crowded beach or park, and the like, or when social distancing is not possible.

Example 10

A series of laboratory experiments can be performed in order to determine a photosensitizer solution or a gel that can provide for multiple hours of virucidal singlet oxygen and other radical species generation in ambient light after a single application.

Example 11

A kit can be provided for users which includes a pre-filled handle containing a photosensitizer solution or gel, with an attached sponge and sponge cover. The kit may optionally contain a spray bottle with a nozzle capable of rapidly dispersing photosensitizing solution or in a wide pattern. The kit also optionally contains a sticker, stick-on pledget, or tape containing an indicator with visible methylene blue. The indicator is affixed to the surface of the wearable item and when the blue color vanishes, indicates to the user that the photosensitizing solution or gel requires reapplication. The kit also optionally contains a vial of skin adhering liquid which is applied to the edges of the public mask, which enables the user to create an improved seal around the edges of the mask during use.

Example 12

As opposed to a single photosensitizer, the use of multiple photosensitizers such as methylene blue, erythrosine, and riboflavin are photoactivated by one or more non-overlapping wavebands in ambient white light or sunlight, which increases the speed and efficiency of virucidal action of the photosensitizer by effectively using more photons per unit time in the ambient light which activates more photosensitizer molecules per unit time, which in turn reduces the infection risk to the user.

Example 13

As opposed to a purely aqueous photosensitizer solution, a photosensitizing gel can improve the adherence of the photosensitizers on surfaces to be disinfected, improves dispersion of the photosensitizer on hydrophobic surfaces, and reduces the risk of droplets being dispersed to the ambient atmosphere where unwanted inhalation may be a risk. Photosensitizers in a gel formulation when sprayed on surfaces will fall rapidly due to gravity.

Example 14

Many members of the public who use public facemasks, purchased, or homemade have the perception that the public facemasks will provide protection from other infected individuals in the vicinity. However, studies have shown that protection of the user using public facemasks may only provide a measure of protection of individuals in the vicinity of the user, from the infected user who is exhaling, or may cough or sneeze into the mask. The use of photosensitizers on public masks will provide enhanced two-way protection of the user and individuals in the vicinity of the user due to the active antiviral action augmenting the intrinsic weak barrier function of the public mask.

The particulars shown herein are by way of example and for purposes of illustrative discussion of the preferred embodiments of the present innovation only and are presented in the cause of providing what is believed to be the most useful and readily understood description of the principles and conceptual aspects of various embodiments of the system. In this regard, no attempt is made to show structural details of the innovation in more detail than is necessary for the fundamental understanding of the innovation, the description taken with the drawings and/or examples making apparent to those skilled in the art how the several forms of the innovation may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments and examples of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments and examples can be combined or substituted for elements in other embodiments and examples. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While illustrative embodiments have been illustrated and described, it will be appreciated that various changes can be made therein without departing from the spirit and scope of the invention.

The invention claimed is:

1. An article that is worn on a person, comprising:
a material forming a part of the article that covers a body part, the material is configured to provide protection from microbes;
one or more photosensitizers are incorporated over an area of the material, wherein the one or more photosensitizers generate singlet oxygen by absorbing light of a particular waveband to provide protection from microbes in combination with the material;
one or more light source incorporated into the article, wherein the light source emits a waveband of light absorbed by the one or more photosensitizers;
a plurality of optical fibers that abut the light source, wherein the plurality of optical fibers are edge-emitting optical light fibers, and the plurality of optical fibers are distributed to emit light over the area of the material incorporated with the one or more photosensitizers; and
a reservoir incorporated into the material, wherein the reservoir contains a solution of the one or more photosensitizers, and the reservoir elutes the photosensitizer solution into the material over time and at a rate that permits renewal of an effective concentration of the one or more photosensitizers.

2. The article of claim 1, wherein the article is a personal protective equipment article selected from a mask, a glove, and a gown.

3. The article of claim 1, wherein the one or more light source includes a lens configured to direct the light onto the area of the material incorporated with the one or more photosensitizers.

4. The article of claim 1, comprising a first and a second light source incorporated into the article, wherein the first light source and the second light source emit a waveband of light absorbed by the one or more photosensitizer, and the first light source and the second light source are positioned at different locations on the article to illuminate the areas of the material incorporated with the one or more photosensitizers.

5. The article of claim 1, wherein at least one edge-emitting optical fiber is bound on a surface of the material incorporating the one or more photosensitizer and at least one edge-emitting optical fiber is within the material incorporating the one or more photosensitizer.

6. The article of claim 1, wherein the material is an optically transparent polymer.

7. The article of claim 1, wherein the one or more photosensitizers include one or more of methylene blue derivative, methylene blue, xanthene dyes and derivatives, chlorophyll derivatives, tetrapyrrole structures, porphyrins, chlorins, bacteriochlorins, phthalocyanines, texaphyrins, prodrugs, aminolevulinic acids, phenothiaziniums, squaraine, boron compounds, transition metal complexes, hypericin, riboflavin, curcumin, titanium dioxide, psoralens, tetracyclines, flavins, riboflavin, riboflavin derivatives, erythrosine, erythrosine derivatives, photosensitizer nanocompositions, or combinations thereof.

* * * * *